(12) United States Patent
Kim et al.

(10) Patent No.: US 9,598,483 B2
(45) Date of Patent: Mar. 21, 2017

(54) MONOCLONAL ANTIBODY BINDING SPECIFICALLY TO DLL4 AND USE THEREOF

(71) Applicant: ABLBIO, Seoul (KR)

(72) Inventors: Eun A. Kim, Daejeon (KR); Sang Kyung Park, Daejeon (KR); Kyung Duk Moon, Daejeon (KR); Dong Heon Lee, Daejeon (KR); Yu Bin Choi, Daejeon (KR); Dong In Kim, Daejeon (KR); Kyung Jae Kang, Daejeon (KR)

(73) Assignee: ABLBIO, Seoul (KR)

( * ) Notice: Subject to any disclaimer, the term of this patent is extended or adjusted under 35 U.S.C. 154(b) by 105 days.

(21) Appl. No.: 14/412,419

(22) PCT Filed: Jul. 2, 2013

(86) PCT No.: PCT/KR2013/005855
§ 371 (c)(1),
(2) Date: Dec. 31, 2014

(87) PCT Pub. No.: WO2014/007513
PCT Pub. Date: Jan. 9, 2014

(65) Prior Publication Data
US 2015/0183856 A1    Jul. 2, 2015

(30) Foreign Application Priority Data

Jul. 2, 2012    (KR) ................. 10-2012-0071996
Jun. 20, 2013    (KR) ................. 10-2013-0071261

(51) Int. Cl.
| | | |
|---|---|---|
| *C07K 16/22* | (2006.01) | |
| *C07K 16/24* | (2006.01) | |
| *A61K 39/395* | (2006.01) | |
| *C07K 16/18* | (2006.01) | |
| *C07K 16/28* | (2006.01) | |
| *G01N 33/577* | (2006.01) | |
| *G01N 33/574* | (2006.01) | |
| *C07K 14/475* | (2006.01) | |
| *C07K 14/52* | (2006.01) | |
| *C07K 14/705* | (2006.01) | |
| *C07K 16/30* | (2006.01) | |
| *A61K 39/00* | (2006.01) | |

(52) U.S. Cl.
CPC .......... *C07K 16/18* (2013.01); *A61K 39/3955* (2013.01); *C07K 16/22* (2013.01); *C07K 16/28* (2013.01); *G01N 33/574* (2013.01); *G01N 33/577* (2013.01); *A61K 39/395* (2013.01); *A61K 2039/505* (2013.01); *C07K 14/475* (2013.01); *C07K 14/52* (2013.01); *C07K 16/24* (2013.01); *C07K 16/30* (2013.01); *C07K 2317/76* (2013.01); *C07K 2317/92* (2013.01); *G01N 2333/4703* (2013.01)

(58) Field of Classification Search
CPC .......... A61K 2039/505; A61K 2300/00; A61K 39/3955; A61K 39/39558; A61K 39/395; A61K 39/39533; C07K 2317/76; C07K 2317/73; C07K 16/18; C07K 2317/56; C07K 2317/565; C07K 16/22; C07K 16/00; C07K 16/24; C07K 2316/96; C07K 14/475; C07K 14/52
See application file for complete search history.

(56) References Cited

U.S. PATENT DOCUMENTS

| 8,192,738 B2 | 6/2012 | Bedian et al. | |
|---|---|---|---|
| 2010/0196385 A1* | 8/2010 | Bedian .................. | C07K 16/22 424/141.1 |
| 2010/0292312 A1 | 11/2010 | Yan et al. | |
| 2011/0117079 A1 | 5/2011 | Benatuil et al. | |
| 2011/0189200 A1 | 8/2011 | Skokos | |
| 2011/0213127 A1 | 9/2011 | Gill et al. | |

(Continued)

FOREIGN PATENT DOCUMENTS

| WO | WO 2008/076379 A2 | 6/2008 |
|---|---|---|
| WO | WO 2011/039368 A2 | 4/2011 |

(Continued)

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*

(Continued)

*Primary Examiner* — Bridget E Bunner
(74) *Attorney, Agent, or Firm* — Hultquist, PLLC; Steven J. Hultquist

(57) ABSTRACT

The present invention relates to a novel monoclonal antibody that binds specifically to delta-like ligand (DLL4), and more particularly to a monoclonal antibody that binds specifically to human delta-like ligand 4 to effectively inhibit the interaction between delta-like ligand 4 and Notch receptor, a polynucleotide encoding the monoclonal antibody, an expression vector comprising the polynucleotide, a transformant comprising the expression vector, a method for preparing the monoclonal antibody, a pharmaceutical composition for preventing or treating cancer comprising the monoclonal antibody, a composition for diagnosing cancer comprising the monoclonal antibody, a method for diagnosing cancer using the monoclonal antibody, and a pharmaceutical composition for preventing or treating autoimmune disease comprising the monoclonal antibody.

13 Claims, 6 Drawing Sheets

(56) References Cited

U.S. PATENT DOCUMENTS

2011/0217237 A1 9/2011 Chen et al.
2011/0318339 A1* 12/2011 Smider .................. C07K 16/00
424/133.1

FOREIGN PATENT DOCUMENTS

WO  WO 2011/050262 A2  4/2011
WO  WO 2011/094465 A1  8/2011

OTHER PUBLICATIONS

Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Tokuriki et al. Stability effects of mutations and protein evolvability. Curr Opin Structural Biol 19: 596-604, 2009.*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
F. Billiard et al: "Dll4-Notch signaling in Flt3-independent dendritic cell development and autoimmunity in mice", J. Exp. Med., vol. 209, No. 5, Apr. 30, 2012, pp. 1011-1028.
N. D. Reynolds et al: "Delta-Like Ligand 4 Regulates Central Nervous System T Cell Accumulation during Experimental Autoimmune Encephalomyelitis", The Journal of Immunology, vol. 187, No. 5, Jul. 25, 2011, pp. 2803-2813.
Waka Ishida et al: "Regulation of Experimental Autoimmune Uveoretinitis by Anti-Delta-Like Ligand 4 Monoclonal Antibody", Investigative Ophthalmology & Visual Science, vol. 52, No. 11, Oct. 1, 2011, pp. 8224-8230.
NCBI GenBank No. BAI54638.1 (Dec. 1, 2009).
NCBI GenBank No. ADM44137.1 (Aug. 31, 2010).
NCBI GenBank No. ABP98628.1 (May 26, 2009).
NCBI GenBank No. ADM43922.1 (Aug. 31, 2010).
Weng et al., "Activating Mutations of NOTCH1 in Human T Cell Acute Lymphoblastic Leukemia," Science, vol. 306, Oct. 8, 2004, pp. 269-271.
Gallahan et al., "Mammary Tumorigenesis in Feral Mice: Identification of a New int Locus in Mouse Mammary Tumor Virus (Czech II)-Induced Mammary Tumors," Journal of Virology, Jan. 1987, vol. 61, No. 1, p. 66-74.
Miele, "Notch Signaling," Molecular Pathways, Clin Cancer Res 2006:12(4), Feb. 15, 2006, p. 1074-1079.
Reedijk et al., "High-level Coexpression of JAG1 and NOTCH1 is Observed in Human Breast Cancer and Is Associated with Poor Overall Survival," Cancer Res 2005; 65:(18) Sep. 15, 2005; pp. 8530-8537.
Santagata et al., "JAGGED1 Expression Is Associated with Prostate Cancer Metastasis and Recurrence," Cancer Research 64, 6854-6857, Oct. 1, 2004.
Reinacher-Schick et al., "Drug Insight: antiangiogenic therapies for gastrointestinal cancers—focus on monoclonal antibodies," Nature Clinical Practice Gastroenterology & Hepatology, May 2008, vol. 5, No. 5.
Li et al., "Delta-like 4 Notch Ligand Regulates Tumor Angiogenesis, Improves Tumor Vascular Function, and Promotes tumor Growth In vivo," Cancer Res 2007; 67:(23) Dec. 1, 2007, pp. 11244-11253.
Noquera-Troise I et al., "Blockade of Dll4 inhibits tumour growth by promoting non-productive angiogenesis," Novartis Found Symp, 2007;283:106-20; discussion 121-5; 238-41; Dec. 21, 2006.
Bassil et al., "Notch Ligand Delta-Like 4 Blockade Alleviates Experimental Autoimmune Encephalomyelitis by Promoting Regulatory T Cell Development," J Immunol 2011; 187:2322-2328.
Hu et al., "Biological Roles of the Delta Family Notch Ligand Dll4 in Tumor and Endothelial Cells in Ovarian Cancer," Cancer Res; 71(18) Sep. 15, 2011; pp. 6030-6039.
Tax et al., "Sequence of C. elegans lag-2 reveals a cell-signalling domain shared with Delta and Serrate of *Drosophila*," Nature, vol. 368, Mar. 10, 1994, pp. 150-154.
International Search Report dated Sep. 23, 2013 for PCT/KR2013/005855 filed Jul. 2, 2013.

* cited by examiner

| CLONE | VH | | | | | | |
|---|---|---|---|---|---|---|---|
| | Frame 1 | CDR1 | Frame 2 | CDR2 | Frame 3 | CDR3 | Frame 4 |
| MLCK-1 (SEQ ID NO.1) | EVQLLESGGGLVQPGGSLRLSCAAS | GFTFSDYAMS (SEQ ID NO.2) | WVRQAPGKGLEWVS | WTYSDDGNKYYADSVKG (SEQ ID NO.3) | RFTISRDNSKNTLYLQMNSLRAEDTAVYYCAR | ADPPDY (SEQ ID NO.4) | WGQGTLVTVSS |
| MLCK-2 (SEQ ID NO.5) | EVQLLESGGGLVQPGGSLRLSCAAS | GFTFSDYAMS (SEQ ID NO.2) | WVRQAPGKGLEWVS | WTYSGSGNKYYADSVKG (SEQ ID NO.6) | RFTISRDNSKNTLYLQMNSLRAEDTAVYYCAR | ADVPPDY (SEQ ID NO.7) | WGQGTLVTVSS |
| MLCK-3 (SEQ ID NO.8) | EVQLLESGGGLVQPGGSLRLSCAAS | GFTFSDYAMS (SEQ ID NO.2) | WVRQAPGKGLEWVS | WTYYDSGNKYYADSVKG (SEQ ID NO.9) | RFTISRDNSKNTLYLQMNSLRAEDTAVYYCAR | ADLPPDY (SEQ ID NO.10) | WGQGTLVTVSS |
| MLCK-4 (SEQ ID NO.11) | EVQLLESGGGLVQPGGSLRLSCAAS | GFTFSNYAMS (SEQ ID NO.12) | WVRQAPGKGLEWVS | WVNHGGGDTYYADSVKG (SEQ ID NO.13) | RFTISRDNSRNTLYLQMNSLRAEDTAVYYCAR | GPNYTFGHPPDY (SEQ ID NO.14) | WGQGTLVTVSS |

| | VL | | | | | | |
|---|---|---|---|---|---|---|---|
| | Frame 1 | CDR1 | Frame 2 | CDR2 | Frame 3 | CDR3 | Frame 4 |
| MLCK-1 (SEQ ID NO.15) | QSVLTQPPSASGTPGQRVTISC | TGSSSNIGSNNVS (SEQ ID NO.16) | WYQQLPGTAPKLLIY | SDNNRPS (SEQ ID NO.17) | GVPDRFSGSKSGTSASLAISGLRSEDEADYYC | ATWDSSLNGYV (SEQ ID NO.18) | FGGGTKLTVL |
| MLCK-2 (SEQ ID NO.19) | QSVLTQPPSASGTPGQRVTISC | TGSSSNIGSNDVT (SEQ ID NO.20) | WYQQLPGTAPKLLIY | ADSKRPS (SEQ ID NO.21) | GVPDRFSGSKSGTSASLAISGLRSEDEADYYC | GTWDASLSGNV (SEQ ID NO.22) | FGGGTKLTVL |
| MLCK-3 (SEQ ID NO.23) | QSVLTQPPSASGTPGQRVTISC | SGSSSNIGNNNAVT (SEQ ID NO.24) | WYQQLPGTAPKLLIY | SDNNRPS (SEQ ID NO.25) | GVPDRFSGSKSGTSASLAISGLRSEDEADYYC | GTWDASLSGNV (SEQ ID NO.26) | FGGGTKLTVL |
| MLCK-4 (SEQ ID NO.27) | QSVLTQPPSASGTPGQRVTISC | RGSPSNIGNNTVY (SEQ ID NO.28) | WYQQLPGTAPKLLIY | SDSQRPS (SEQ ID NO.29) | GVPDRFSGSKSGTSASLAISGLRSEDEADYYC | GSWDYSLSAYV (SEQ ID NO.30) | FGGGTKLTVL |

FIGURE 1

SEQUENCE LISTING

```
<160> NUMBER OF SEQ ID NOS: 35

<210> SEQ ID NO 1
<211> LENGTH: 116
<212> TYPE: PRT
<213> ORGANISM: Artificial Sequence
<220> FEATURE:
<223> OTHER INFORMATION: a heavy chain variable region of MLCK-1

<400> SEQUENCE: 1

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Ala Met Ser Trp Val Arg Gln Ala Pro Gly Lys Gly Leu Glu Trp Val
         35                  40                  45

Ser Trp Ile Tyr Ser Asp Asp Gly Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Asp Pro Pro Phe Asp Tyr Trp Gly Gln Gly Thr Leu Val
            100                 105                 110

Thr Val Ser Ser
        115

<210> SEQ ID NO 2
<211> LENGTH: 10
<212> TYPE: PRT
<213> ORGANISM: Artificial Sequence
<220> FEATURE:
```

<223> OTHER INFORMATION: CDR1 of a heavy chain variable region of
      MLCK-1, 2, 3

<400> SEQUENCE: 2

Gly Phe Thr Phe Ser Asp Tyr Ala Met Ser
 1               5                  10

<210> SEQ ID NO 3
<211> LENGTH: 17
<212> TYPE: PRT
<213> ORGANISM: Artificial Sequence
<220> FEATURE:
<223> OTHER INFORMATION: CDR2 of a heavy chain variable region of MLCK-1

<400> SEQUENCE: 3

Trp Ile Tyr Ser Asp Asp Gly Asn Lys Tyr Tyr Ala Asp Ser Val Lys
 1               5                  10                  15

Gly

<210> SEQ ID NO 4
<211> LENGTH: 7
<212> TYPE: PRT
<213> ORGANISM: Artificial Sequence
<220> FEATURE:
<223> OTHER INFORMATION: CDR3 of a heavy chain variable region of MLCK-1

<400> SEQUENCE: 4

Ala Asp Pro Pro Phe Asp Tyr
 1               5

<210> SEQ ID NO 5
<211> LENGTH: 116
<212> TYPE: PRT
<213> ORGANISM: Artificial Sequence
<220> FEATURE:
<223> OTHER INFORMATION: a heavy chain variable region of MLCK-2

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Trp Ile Tyr Ser Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Trp Pro Phe Asp Tyr Trp Gly Gln Gly Thr Leu Val
            100                 105                 110

Thr Val Ser Ser
        115

<210> SEQ ID NO 6
<211> LENGTH: 17
<212> TYPE: PRT
<213> ORGANISM: Artificial Sequence
<220> FEATURE:
<223> OTHER INFORMATION: CDR2 of a heavy chain variable region of MLCK-2

<400> SEQUENCE: 6

```
Trp Ile Tyr Ser Gly Ser Gly Asn Lys Tyr Tyr Ala Asp Ser Val Lys
  1               5                  10                  15
Gly

<210> SEQ ID NO 7
<211> LENGTH: 7
<212> TYPE: PRT
<213> ORGANISM: Artificial Sequence
<220> FEATURE:
<223> OTHER INFORMATION: CDR3 of a heavy chain variable region of MLCK-2

<400> SEQUENCE: 7

Ala Asp Trp Pro Phe Asp Tyr
  1               5

<210> SEQ ID NO 8
<211> LENGTH: 116
<212> TYPE: PRT
<213> ORGANISM: Artificial Sequence
<220> FEATURE:
<223> OTHER INFORMATION: a heavy chain variable region of MLCK-3

<400> SEQUENCE: 8

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Ala Met Ser Trp Val Arg Gln Ala Pro Gly Lys Gly Leu Glu Trp Val
         35                  40                  45

Ser Trp Ile Tyr Tyr Asp Ser Gly Ser Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Asp Leu Pro Phe Asp Tyr Trp Gly Gln Gly Thr Leu Val
            100                 105                 110

Thr Val Ser Ser
        115

<210> SEQ ID NO 9
<211> LENGTH: 17
<212> TYPE: PRT
<213> ORGANISM: Artificial Sequence
<220> FEATURE:
<223> OTHER INFORMATION: CDR2 of a heavy chain variable region of MLCK-3

<400> SEQUENCE: 9

Trp Ile Tyr Tyr Asp Ser Gly Ser Lys Tyr Tyr Ala Asp Ser Val Lys
  1               5                  10                  15
Gly

<210> SEQ ID NO 10
<211> LENGTH: 7
<212> TYPE: PRT
<213> ORGANISM: Artificial Sequence
<220> FEATURE:
<223> OTHER INFORMATION: CDR3 of a heavy chain variable region of MLCK-3

<400> SEQUENCE: 10

Ala Asp Leu Pro Phe Asp Tyr
```

```
<210> SEQ ID NO 11
<211> LENGTH: 121
<212> TYPE: PRT
<213> ORGANISM: Artificial Sequence
<220> FEATURE:
<223> OTHER INFORMATION: a heavy chain variable region of MLCK-4

<400> SEQUENCE: 11

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Trp Ile Tyr His Gly Gly Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Pro Asn Tyr Thr Phe Gly Lys Pro Phe Asp Tyr Trp Gly
            100                 105                 110

Gln Gly Thr Leu Val Thr Val Ser Ser
        115                 120

<210> SEQ ID NO 12
<211> LENGTH: 10
<212> TYPE: PRT
<213> ORGANISM: Artificial Sequence
<220> FEATURE:
<223> OTHER INFORMATION: CDR1 of a heavy chain variable region of MLCK-4

<400> SEQUENCE: 12

Gly Phe Thr Phe Ser Asn Tyr Ala Met Ser
 1               5                  10

<210> SEQ ID NO 13
<211> LENGTH: 17
<212> TYPE: PRT
<213> ORGANISM: Artificial Sequence
<220> FEATURE:
<223> OTHER INFORMATION: CDR2 of a heavy chain variable region of MLCK-4

<400> SEQUENCE: 13

Trp Ile Tyr His Gly Gly Asp Thr Tyr Tyr Ala Asp Ser Val Lys
 1               5                  10                  15

Gly

<210> SEQ ID NO 14
<211> LENGTH: 12
<212> TYPE: PRT
<213> ORGANISM: Artificial Sequence
<220> FEATURE:
<223> OTHER INFORMATION: CDR3 of a heavy chain variable region of MLCK-4

<400> SEQUENCE: 14

Gly Pro Asn Tyr Thr Phe Gly Lys Pro Phe Asp Tyr
 1               5                  10

<210> SEQ ID NO 15
```

```
<211> LENGTH: 110
<212> TYPE: PRT
<213> ORGANISM: Artificial Sequence
<220> FEATURE:
<223> OTHER INFORMATION: a light chain variable region of MLCK-1

<400> SEQUENCE: 15

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Asn Ile Gly Ser Asn
            20                  25                  30

Asn Val Ser Trp Tyr Gln Gln Leu Pro Gly Thr Ala Pro Lys Leu Leu
        35                  40                  45

Ile Tyr Ser Asp Asn Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Ser Ser Leu
                85                  90                  95

Asn Gly Tyr Val Phe Gly Gly Gly Thr Lys Leu Thr Val Leu
            100                 105                 110

<210> SEQ ID NO 16
<211> LENGTH: 13
<212> TYPE: PRT
<213> ORGANISM: Artificial Sequence
<220> FEATURE:
<223> OTHER INFORMATION: CDR1 of a light chain variable region of MLCK-1

<400> SEQUENCE: 16

Thr Gly Ser Ser Ser Asn Ile Gly Ser Asn Asn Val Ser
 1               5                  10

<210> SEQ ID NO 17
<211> LENGTH: 7
<212> TYPE: PRT
<213> ORGANISM: Artificial Sequence
<220> FEATURE:
<223> OTHER INFORMATION: CDR2 of a light chain variable region of MLCK-1

<400> SEQUENCE: 17

Ser Asp Asn Asn Arg Pro Ser
 1               5

<210> SEQ ID NO 18
<211> LENGTH: 11
<212> TYPE: PRT
<213> ORGANISM: Artificial Sequence
<220> FEATURE:
<223> OTHER INFORMATION: CDR3 of a light chain variable region of MLCK-1

<400> SEQUENCE: 18

Ala Thr Trp Asp Ser Ser Leu Asn Gly Tyr Val
 1               5                  10

<210> SEQ ID NO 19
<211> LENGTH: 110
<212> TYPE: PRT
<213> ORGANISM: Artificial Sequence
<220> FEATURE:
<223> OTHER INFORMATION: a light chain variable region of MLCK-2

<400> SEQUENCE: 19

Gln Ser Val Leu Thr Gln Pro Pro Ser Ala Ser Gly Thr Pro Gly Gln
```

```
                1               5                   10                  15
            Arg Val Thr Ile Ser Cys Thr Gly Ser Ser Ser Asn Ile Gly Ser Asn
                            20                  25                  30

Asp Val Thr Trp Tyr Gln Gln Leu Pro Gly Thr Ala Pro Lys Leu Leu
                        35                  40                  45

Ile Tyr Ala Asp Ser Lys Arg Pro Ser Gly Val Pro Asp Arg Phe Ser
                    50                  55                  60

Gly Ser Lys Ser Gly Thr Ser Ala Ser Leu Ala Ile Ser Gly Leu Arg
                65                  70                  75                  80

Ser Glu Asp Glu Ala Asp Tyr Tyr Cys Gly Thr Trp Asp Tyr Ser Leu
                            85                  90                  95

Ser Ala Tyr Val Phe Gly Gly Gly Thr Lys Leu Thr Val Leu
                            100                 105                 110

<210> SEQ ID NO 20
<211> LENGTH: 13
<212> TYPE: PRT
<213> ORGANISM: Artificial Sequence
<220> FEATURE:
<223> OTHER INFORMATION: CDR1 of a light chain variable region of MLCK-2

<400> SEQUENCE: 20

Thr Gly Ser Ser Ser Asn Ile Gly Ser Asn Asp Val Thr
 1               5                   10

<210> SEQ ID NO 21
<211> LENGTH: 7
<212> TYPE: PRT
<213> ORGANISM: Artificial Sequence
<220> FEATURE:
<223> OTHER INFORMATION: CDR2 of a light chain variable region of MLCK-2

<400> SEQUENCE: 21

Ala Asp Ser Lys Arg Pro Ser
 1               5

<210> SEQ ID NO 22
<211> LENGTH: 11
<212> TYPE: PRT
<213> ORGANISM: Artificial Sequence
<220> FEATURE:
<223> OTHER INFORMATION: CDR3 of a light chain variable region of MLCK-2

<400> SEQUENCE: 22

Gly Thr Trp Asp Tyr Ser Leu Ser Ala Tyr Val
 1               5                   10

<210> SEQ ID NO 23
<211> LENGTH: 110
<212> TYPE: PRT
<213> ORGANISM: Artificial Sequence
<220> FEATURE:
<223> OTHER INFORMATION: a light chain variable region of MLCK-3

<400> SEQUENCE: 23

Gln Ser Val Leu Thr Gln Pro Pro Ser Ala Ser Gly Thr Pro Gly Gln
 1               5                   10                  15

Arg Val Thr Ile Ser Cys Ser Gly Ser Ser Ser Asn Ile Gly Asn Asn
                20                  25                  30

Ala Val Thr Trp Tyr Gln Gln Leu Pro Gly Thr Ala Pro Lys Leu Leu
            35                  40                  45

Ile Tyr Ser Asp Asn His Arg Pro Ser Gly Val Pro Asp Arg Phe Ser
```

```
                50                  55                  60
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Ala Ser Leu
                 85                  90                  95

Ser Gly Tyr Val Phe Gly Gly Gly Thr Lys Leu Thr Val Leu
                100                 105                 110

<210> SEQ ID NO 24
<211> LENGTH: 13
<212> TYPE: PRT
<213> ORGANISM: Artificial Sequence
<220> FEATURE:
<223> OTHER INFORMATION: CDR1 of a light chain variable region of MLCK-3

<400> SEQUENCE: 24

Ser Gly Ser Ser Ser Asn Ile Gly Asn Asn Ala Val Thr
 1               5                  10

<210> SEQ ID NO 25
<211> LENGTH: 7
<212> TYPE: PRT
<213> ORGANISM: Artificial Sequence
<220> FEATURE:
<223> OTHER INFORMATION: CDR2 of a light chain variable region of MLCK-3

<400> SEQUENCE: 25

Ser Asp Asn His Arg Pro Ser
 1               5

<210> SEQ ID NO 26
<211> LENGTH: 11
<212> TYPE: PRT
<213> ORGANISM: Artificial Sequence
<220> FEATURE:
<223> OTHER INFORMATION: CDR3 of a light chain variable region of MLCK-3

<400> SEQUENCE: 26

Gly Thr Trp Asp Ala Ser Leu Ser Gly Tyr Val
 1               5                  10

<210> SEQ ID NO 27
<211> LENGTH: 110
<212> TYPE: PRT
<213> ORGANISM: Artificial Sequence
<220> FEATURE:
<223> OTHER INFORMATION: a light chain variable region of MLCK-4

<400> SEQUENCE: 27

Gln Ser Val Leu Thr Gln Pro Pro Ser Ala Ser Gly Thr Pro Gly Gln
 1               5                  10                  15

Arg Val Thr Ile Ser Cys Arg Gly Ser Pro Ser Asn Ile Gly Asn Asn
                20                  25                  30

Thr Val Tyr Trp Tyr Gln Gln Leu Pro Gly Thr Ala Pro Lys Leu Leu
            35                  40                  45

Ile Tyr Ser Asp Ser Gln Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Ala Tyr Val Phe Gly Gly Gly Thr Lys Leu Thr Val Leu
```

<210> SEQ ID NO 28
<211> LENGTH: 13
<212> TYPE: PRT
<213> ORGANISM: Artificial Sequence
<220> FEATURE:
<223> OTHER INFORMATION: CDR1 of a light chain variable region of MLCK-4

<400> SEQUENCE: 28

Arg Gly Ser Pro Ser Asn Ile Gly Asn Asn Thr Val Tyr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CDR2 of a light chain variable region of MLCK-4

<400> SEQUENCE: 29

Ser Asp Ser Gln Arg Pro Ser
1               5

<210> SEQ ID NO 30
<211> LENGTH: 11
<212> TYPE: PRT
<213> ORGANISM: Artificial Sequence
<220> FEATURE:
<223> OTHER INFORMATION: CDR3 of a light chain variable region of MLCK-4

<400> SEQUENCE: 30

Gly Ser Trp Asp Tyr Ser Leu Ser Ala Tyr Val
1               5                   10

<210> SEQ ID NO 31
<211> LENGTH: 330
<212> TYPE: PRT
<213> ORGANISM: Artificial Sequence
<220> FEATURE:
<223> OTHER INFORMATION: a heavy chain constant region of IgG1

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp

```
                145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 326
<212> TYPE: PRT
<213> ORGANISM: Artificial Sequence
<220> FEATURE:
<223> OTHER INFORMATION: a heavy chain constant region of IgG2

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
                130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
```

```
                    180                 185                 190
Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 33
<211> LENGTH: 377
<212> TYPE: PRT
<213> ORGANISM: Artificial Sequence
<220> FEATURE:
<223> OTHER INFORMATION: a heavy chain constant region of IgG3

<400> SEQUENCE: 33

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
```

```
                210                 215                 220
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 34
<211> LENGTH: 327
<212> TYPE: PRT
<213> ORGANISM: Artificial Sequence
<220> FEATURE:
<223> OTHER INFORMATION: a heavy chain constant region of IgG4

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

-continued

```
                195                 200                 205
Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 35
<211> LENGTH: 105
<212> TYPE: PRT
<213> ORGANISM: Artificial Sequence
<220> FEATURE:
<223> OTHER INFORMATION: a constant region of lamda light chain

<400> SEQUENCE: 35

Gln Pro Lys Ala Ala Pro Ser Val Thr Leu Phe Pro Pro Ser Ser Glu
  1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Ala Glu Cys Ser
            100                 105
```

MONOCLONAL ANTIBODY BINDING SPECIFICALLY TO DLL4 AND USE THEREOF

This application is a U.S. national phase application of International Patent Application No. PCT/KR2013/005855 filed on Jul. 2, 2013, which claims the benefit of Korean patent application 10-2012-0071996, filed Jul. 2, 2012 and Korean patent application 10-2013-0071261, filed Jun. 20, 2013.

TECHNICAL FIELD

The present invention relates to a novel monoclonal antibody that binds specifically to delta-like ligand 4 (DLL4), and more particularly to a monoclonal antibody that binds specifically to human delta-like ligand 4 to effectively inhibit the binding between delta-like ligand 4 and Notch receptor, a polynucleotide encoding the monoclonal antibody, an expression vector comprising the polynucleotide, a transformant comprising the expression vector, a method for preparing the monoclonal antibody, a pharmaceutical composition for preventing or treating cancer comprising the monoclonal antibody, a composition for diagnosing cancer comprising the monoclonal antibody, a method for diagnosing cancer using the monoclonal antibody, and a pharmaceutical composition for preventing or treating autoimmune disease comprising the monoclonal antibody.

BACKGROUND ART

It was reported that Notch signaling is an evolutionarily highly conserved in vertebrate and invertebrate animals and plays a very pivotal role in determining the fate of cells in the initial stage of development. Notch signaling is known as a major factor that regulates the differentiation of neural cells, intraocular cells, lymphocytes, muscular cells, hematocytes and the like and is also involved in the development of blood vessels. Mammals have four Notch receptors (Notch 1, 2, 3 and 4), and each of Notch receptors is synthesized as a protein having a size of 300-350 kDa and cleaved at the S1 site by furin-like convertase in the Golgi to form a heterodimer on the cell surface. In addition, four Notch ligands (jagged-1/2 and delta-like ligand (DLL) 1/3/4) were found in mammals.

The Notch receptors and ligands are all membrane proteins and bind at the interface between two adjacent cells to induce Notch signaling. When cells come into contact with each other, the extracellular domains come into direct contact with each other to induce signaling, and cell responses that differ depending on combinations of ligands and receptors appear. When ligands and Notch receptors bind to each other in Notch signaling, the Notch receptors are structurally changed, and then undergo two sequential proteolytic cleavages. The first proteolytic cleavage begins with the cleavage of the extracellular domain (S2 site) by the metalloprotease ADAM10/17 (a disintegrin and metalloprotease 10/17)/TACE (TNF-α converting enzyme). When the S2 site is cleaved, the S3 site of transmembrane domain of the Notch receptor is then cleaved. The second proteolytic cleavage is mediated by a γ-secretase complex having five subunits. The γ-secretase complex is composed of presenilin 1, presenilin 2, nicastrin, Pen-2, and Aph1. After the two proteolytic cleavages, the Notch intracellular domain (NICD) is released and migrates into the nucleus. In the nucleus, the NICD binds to the transcriptional suppressor CSL (CBF-1/Suppressor of Hairless/Lag-1) to replace the corepressor (CoR) that has been bound to the CSL. The NICD/CSL complex recruits the co-activator (CoA) MAML (mastermind-like) or p300 to activate and induce the expression of Notch target genes such as cyclin D1, p21, NF-κB, c-Myc, pre-Tα (pre-T cell receptor alpha chain), GATA3, NRARP and Deltex1.

Activated Notch signaling is known to induce tumorigenesis in various tumor models. When the activated Notch NICD was expressed in rat hematopoietic cells, T-cell leukemia/lymphomas occurred and about 50% of activated Notch 1 was found in about 50% of T-ALL (T-cell acute lymphoblastic leukemia) (Weng A P et al., Science 2004; 306:71-269). In addition, in the case of breast cancer, Notch 4 receptor was found to be overexpressed in rats (Czech II) introduced with MMTV (mouse mammary tumor virus), and the occurrence of a mammary gland tumor in these rats was reported (Gallahan D et al., Journal of Virology 1987; 61:66-74). It was reported that Notch receptors and ligands and Notch signaling targets are activated in various cancers such as cervical cancer, lung cancer, pancreatic cancer, ovarian cancer, breast cancer and prostate cancer (Miele L et al., Clin Cancer Research 2006; 12(4):1074-79), and it is known that Notch 1 receptor is associated with worse prognosis on breast cancer patients (Reedijk M et al., Cancer Research 2005; 65:8530-7) and associated with the metastasis of prostate cancer (Santagata S et al., Cancer Research 2004; 64:6854-7).

Delta-like 4 (Dl4) or delta-like ligand 4 (DLL4) (hereinafter referred to as "DLL4") is one of delta-class ligands that bind to Notch proteins which are overexpressed in vascular endothelial cells. It is known as a major factor that regulates angiogenesis. DLL4 particularly binds to Notch 1 or Notch 4 receptor which is overexpressed in vascular endothelial cells. It is known that DLL4 is highly overexpressed in cancer blood vessels, although it is also expressed in normal blood vessels (Reinacher-Schick A et al., Nat Clin Pract Gastroenterol Hepatol 2008; 5(5):250-67). Angiogenesis refers to the mechanism by which new blood vessels are formed from the pre-existing blood vessels. Particularly, in tumors, angiogenesis is caused by angiogenic factors such as VEGF in order to supply oxygen and nutrients to the hypoxia area of cancer tissue. It is known that angiogenesis in tumors plays an important role not only in the growth of the tumor, but also in the metastasis of the tumor. When Notch signaling by DLL4 in tumors is blocked, angiogenesis cannot be easily controlled, and thus the growth of the tumors can be inhibited. In addition, when Notch signaling by DLL4 is inhibited, autoimmune disease can be treated by increasing the number of regulatory T cells (Treg) (US Patent Publication No. 2011-0189200). For these reasons, DLL4 becomes a new target in the treatment of cancers and autoimmune diseases.

In order to treat cancer or autoimmune disease by targeting DLL4, studies on the inhibition of Notch signaling in various portions have been conducted. Examples thereof include the receptor decoy that interferes with Notch/ligand bindings, a γ-secretase inhibitor that is involved in the cleavage of Notch proteins in Notch signaling, and miRNA or siRNA for inhibiting either proteins involved in Notch signaling or Notch target genes. Among these various methods for inhibiting Notch signaling, studies on monoclonal antibodies that bind Notch ligands capable of acting in the initial stage of Notch signaling have been of increasing importance. Particularly, for clinical studies, there has been a demand for the development of a human monoclonal antibody which can bind specifically to human DLL4 and can effectively inhibit DLL4/Notch receptor interactions while minimizing the risk of immunogenicity.

DISCLOSURE OF INVENTION

Technical Problem

Accordingly, the present inventors have made extensive efforts to develop a human monoclonal antibody which can bind specifically to human DLL4 and, at the same time, can effectively inhibit DLL4/Notch receptor interactions and can minimize the risk of immunogenicity. As a result, the present inventors have constructed a human monoclonal antibody that specifically binds to human DLL4 wherein the heavy chain and light chain domains are all of human origin from human antibiotic library, and have found that the human monoclonal antibody can effectively inhibit the interaction between DLL4 and Notch protein, and thus can be effectively used for the treatment of diseases such as cancer, thereby completing the present invention.

Solution to Problem

It is an object of the present invention to provide a novel monoclonal antibody which binds specifically to human delta-like ligand 4 (DLL4) and, at the same time, inhibits the interaction between human delta-like ligand 4 and Notch receptor.

Another object of the present invention is to provide a polynucleotide encoding the above monoclonal antibody, an expression vector comprising the polynucleotide, and a transformant comprising the expression vector.

Still another object of the present invention is to provide a method for preparing the above monoclonal antibody.

Still another object of the present invention is to provide a pharmaceutical composition for treating cancer comprising the above monoclonal antibody.

Still another object of the present invention is to provide a method for treating cancer using the above monoclonal antibody.

Still another object of the present invention is to provide a method for diagnosing cancer, the method comprising a step of detecting a delta-like ligand 4 (DLL4) protein in a biological sample, isolated from a subject suspected of having cancer, by an antigen-antibody reaction using the above monoclonal antibody.

Still another object of the present invention is to provide a composition for diagnosing cancer comprising the above monoclonal antibody.

Still another object of the present invention is to provide a kit for diagnosing cancer comprising the above composition for diagnosing cancer.

Still another object of the present invention is to provide a pharmaceutical composition for treating autoimmune disease comprising the above monoclonal antibody.

Still another object of the present invention is to provide a method for treating autoimmune disease using the above monoclonal antibody.

Advantageous Effects of Invention

The human monoclonal antibody according to the present invention shows a strong affinity for human DLL4 and effectively inhibits the binding of DLL4 to Notch receptor, and shows low immunogenicity because the heavy chain and light chain domains thereof are all of human origin. Thus, the human monoclonal antibody of the present invention can be effectively used for the diagnosis and treatment of diseases such as cancer or autoimmune disease.

BRIEF DESCRIPTION OF DRAWINGS

FIG. 1 shows the amino acid sequences of the heavy chain variable region and light chain variable region of a monoclonal antibody to DLL4. In FIG. 1, the frame refers to a framework region, and the CDR refers to a complementarity-determining region.

BEST MODE FOR CARRYING OUT THE INVENTION

Figure 2:
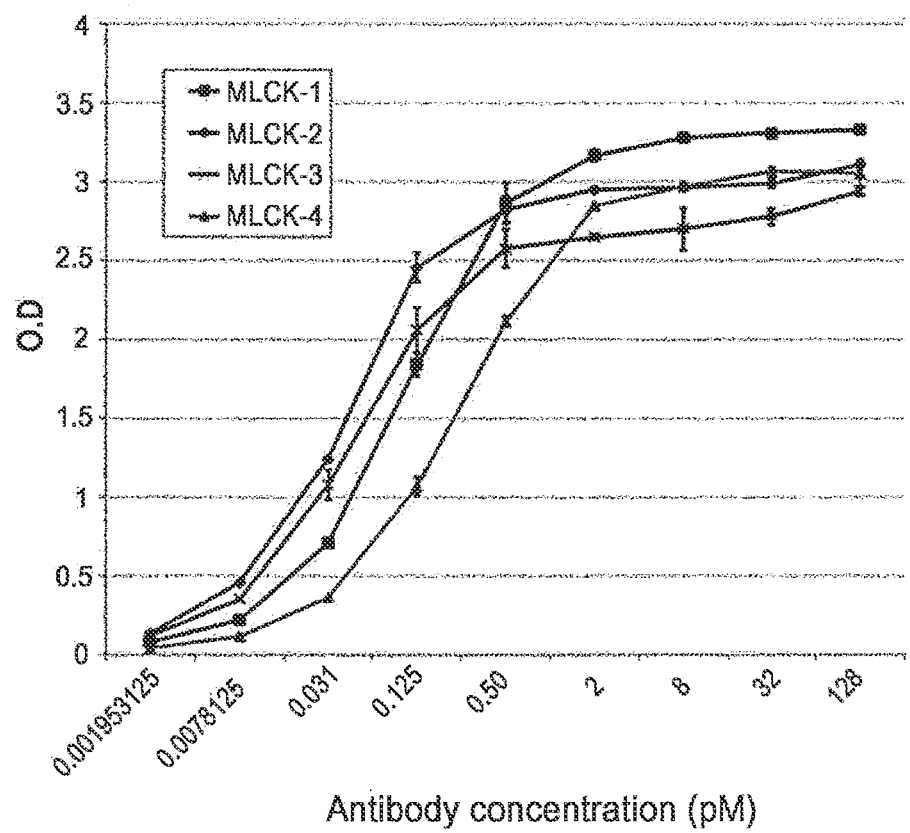
FIG. 2 shows the results of an enzyme-linked immunosorbent assay (ELISA) conducted to examine the abilities of monoclonal antibodies to bind to DLL4.

In one aspect, the present invention provides a novel monoclonal antibody, particularly a human monoclonal antibody, which binds specifically to human delta-like ligand 4 (DLL4) while inhibiting the interaction between human delta-like ligand 4 and Notch receptor.

As used herein, the term "antibody" refers to a protein molecule functioning as a receptor that specifically recognizes an antigen, and includes an immunoglobulin molecule immunologically reactive with a specific antigen. The term also includes polyclonal antibodies, monoclonal antibodies, whole antibodies and antibody fragments. Further, the term also include chimeric antibodies (for example, humanized murine antibodies), bivalent or bispecific molecules (for example, bispecific antibodies), dibodies, triabodies and tetrabodies. The whole antibodies have two full-length light chains and two full-length heavy chains, and each of the light chains is linked to the heavy chain by a disulfide bond. The whole antibodies include IgA, IgD, IgE, IgM and IgG, and IgG has subtypes, including $IgG_1$, $IgG_2$, $IgG_3$ and $IgG_4$. The antibody fragments refer to fragments having a function of binding to antigens and include Fab, Fab', F(ab')$_2$ and Fv. Fab has light chain and heavy chain variable regions, a light chain constant region and a first heavy chain constant region (CH1 domain) and includes one antigen-binding site. Fab' differs from Fab in that it has a hinge region including at least cysteine residue in the C-terminal region of the heavy chain CH1 domain. F(ab')$_2$ antibody is prepared by a disulfide bond between cysteine residues in the hinge region of Fab'. Fv (variable fragment) refers to the minimum antibody fragment having only a heavy chain variable region and a light chain variable region. Double-stranded Fv (dsFv) has a heavy chain variable region linked to a light chain variable region by a disulfide bond, and single-chain Fv (scFv) generally has a heavy chain variable region covalently linked to a light chain variable region by a peptide linker. Such antibody fragments can be obtained using proteases (for example, Fab fragments can be obtained by cleaving whole antibody with papain, and F(ab')$_2$ fragments can be obtained by cleaving whole antibody with pepsin). Preferably, the antibody fragments can be constructed by genetic recombination technology.

As used herein, the term "monoclonal antibody" refers to antibody molecules having a single molecular composition, obtained from a population of essentially identical antibodies. This monoclonal antibody shows a single binding specificity and affinity for a specific epitope.

Typically, an immunoglobulin has a heavy chain and a light chain. Each of the heavy and light chains contains a constant region and a variable region (the regions are also known as "domains"). light chain and heavy chain variable regions contain four framework regions interrupted by three hypervariable regions, also called "complementarity-determining regions" (hereinafter referred to as "CDRs"). The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

As used herein, the term "human antibody" refers to a molecule derived from human immunoglobulin, in which the full-length amino acid sequence of the antibody, including complementarity-determining regions and framework regions, consists of the amino acid sequence of human immunoglobulin. Human antibodies are generally used for the treatment of human diseases and may have three or more potent advantages. First, the human antibody can more easily interact with the human immune system so that target cells can be more efficiently destroyed by, for example, complement-dependent cytotoxicity (CDC) or antibody-dependent cell-mediated cytotoxicity (ADCC). Second, there is an advantage in that the human immune system does not recognize the antibody as an external antibody. Third, there is an advantage in that, even when the antibody is administered in a smaller mount at a lower frequency, the half life thereof in the human circulatory system is similar to that of a naturally occurring antibody. Thus, the human monoclonal antibodies according to the present invention show a strong affinity for DLL4, effectively inhibit the binding of Notch 1 or Notch 4 receptor to cells (e.g., cancer cells) expressing DLL4, and also show low immunogenicity because the heavy chain and light chain domains thereof are all of human origin. Thus, the monoclonal antibodies of the present invention can be effectively used for the treatment of diseases such as cancer or autoimmune disease.

As used herein, the phrase "monoclonal antibody that binds specifically to human delta-like ligand 4 (DLL4)" refers to an antibody that can bind to DLL4 to inhibit the biological activity of DLL4, and it can be used interchangeably with "anti-DLL4 antibody" in the present invention. The monoclonal antibody that binds specifically to DLL4 is not limited, as long as it binds specifically to DLL4 to inhibit the interaction between DLL4 and Notch receptors. Examples of the monoclonal antibody include whole antibodies and antibody fragments as described above. The monoclonal antibody of the present invention can bind specifically to human DLL4 while inhibiting the interaction between DLL4 and Notch proteins, and thus can be effectively used for the treatment of diseases such as cancer or autoimmune disease, in which Notch signaling is involved.

The monoclonal antibody that binds specifically to DLL4 may preferably be a monoclonal antibody, which comprises a heavy chain CDR1 set forth in SEQ ID NO: 2 and binds specifically to DLL4, but is not limited thereto.

The monoclonal antibody comprising the heavy chain CDR1 set forth in SEQ ID NO: 2 may preferably be a monoclonal antibody comprising a heavy chain variable region comprising a heavy chain CDR1 set forth in SEQ ID NO: 2; a heavy chain CDR2 set forth in SEQ ID NO: 3; and a heavy chain CDR3 set forth in SEQ ID NO: 4, and a light chain variable region comprising a light chain CDR1 set forth in SEQ ID NO: 16; a light chain CDR2 set forth in SEQ ID NO: 17; and a light chain CDR3 set forth in SEQ ID NO: 18. More preferably, the monoclonal antibody comprising the heavy chain CDR1 set forth in SEQ ID NO: 2 may be a monoclonal antibody comprising an amino acid sequence of heavy chain variable region set forth in SEQ ID NO: 1 and an amino acid sequence of light chain variable region set forth in SEQ ID NO: 15, but is not limited thereto. In an example of the present invention, the human monoclonal antibody comprising the heavy chain variable region having the amino acid sequence set forth in SEQ ID NO: 1 and the light chain variable region having the amino acid sequence set forth in SEQ ID NO: 15 was named "MLCK-1".

In addition, the monoclonal antibody comprising the heavy chain CDR1 set forth in SEQ ID NO: 2 may preferably be a monoclonal antibody comprising a heavy chain variable region comprising a heavy chain CDR1 set forth in SEQ ID NO: 2; a heavy chain CDR2 set forth in SEQ ID NO: 6; and a heavy chain CDR3 set forth in SEQ ID NO: 7, and a light chain variable region comprising a light chain CDR1 set forth in SEQ ID NO: 20; a light chain CDR2 set forth in SEQ ID NO: 21; and a light chain CDR3 set forth in SEQ ID NO: 22. More preferably, the monoclonal antibody comprising the heavy chain CDR1 set forth in SEQ ID NO: 2 may be a monoclonal antibody comprising an amino acid sequence of heavy chain variable region set forth in SEQ ID NO: 5 and an amino acid sequence of a light chain variable region set forth in SEQ ID NO: 19, but is not limited thereto. In an example of the present invention, the human monoclonal antibody comprising the heavy chain variable region having the amino acid sequence set forth in SEQ ID NO: 5 and the light chain variable region having the amino acid sequence set forth in SEQ ID NO: 19 was named "MLCK-2".

In addition, the monoclonal antibody comprising the heavy chain CDR1 set forth in SEQ ID NO: 2 may preferably be a monoclonal antibody comprising a heavy chain variable region comprising a heavy chain CDR1 set forth in SEQ ID NO: 2; a heavy chain CDR2 set forth in SEQ ID NO: 9; and a heavy chain CDR3 set forth in SEQ ID NO: 10, and a light chain variable region comprising a light chain CDR1 set forth in SEQ ID NO: 24; a light chain CDR2 set forth in SEQ ID NO: 25; and a light chain CDR3 set forth in SEQ ID NO: 26. More preferably, the monoclonal antibody comprising the heavy chain CDR1 set forth in SEQ ID NO: 2 may be a monoclonal antibody comprising a heavy chain variable region amino acid sequence set forth in SEQ ID NO: 8 and a light chain variable region amino acid sequence set forth in SEQ ID NO: 23, but is not limited thereto. In an example of the present invention, the human monoclonal antibody comprising the heavy chain variable region having the amino acid sequence set forth in SEQ ID NO: 8 and the light chain variable region having the amino acid sequence set forth in SEQ ID NO: 23 was named "MLCK-3".

In addition, the monoclonal antibody that binds specifically to DLL4 may preferably be a monoclonal antibody comprising a heavy chain variable region comprising a heavy chain CDR1 set forth in SEQ ID NO: 12; a heavy chain CDR2 set forth in SEQ ID NO: 13; and a heavy chain CDR3 set forth in SEQ ID NO: 14, and a light chain variable region comprising a light chain CDR1 set forth in SEQ ID NO: 28; a light chain CDR2 set forth in SEQ ID NO: 29; and a light chain CDR3 set forth in SEQ ID NO: 30. More preferably, it may be a monoclonal antibody comprising a heavy chain variable region amino acid sequence set forth in SEQ ID NO: 11 and a light chain variable region amino acid sequence set forth in SEQ ID NO: 27, but is not limited thereto. In an example of the present invention, the human monoclonal antibody comprising the heavy chain variable region having the amino acid sequence set forth in SEQ ID NO: 11 and the light chain variable region having the amino acid sequence set forth in SEQ ID NO: 27 was named "MLCK-4".

The sequences of the heavy chain and light chain variable regions of MLCK-1, MLCK-2, MLCK-3 and MLCK-4 are shown in FIG. 1.

When the human monoclonal antibody of the present invention comprises a constant region, it may comprise a constant region derived from IgG, IgA, IgD, IgE, IgM, or combinations or hybrids thereof.

As used herein, the term "combination" means that polypeptides encoding single-chain immunoglobulin constant regions of the same origin are linked to a single-chain polypeptide of a different origin to form a dimer or a multimer. For example, a dimer or a multimer may be formed from two or more constant regions selected from the group consisting of IgG, IgA, IgD, IgE and IgM constant regions.

As used herein, the term "hybrid" means that sequences encoding two or more immunoglobulin heavy chain constant regions of different origins are present in a single-chain immunoglobulin heavy chain constant region. For example, domain hybrids may be composed of 1 to 4 domains selected from CH1, CH2, CH3 and CH4 of IgG, IgA, IgD, IgE and IgM.

Meanwhile, combinations or hybrids of $IgG_1$, $IgG_2$, $IgG_3$, and $IgG_4$ heavy chain constant regions, which are subtypes of IgG, are also possible. These combinations and hybrids are as described above. The $IgG_1$ heavy chain constant region may be an $IgG_1$ heavy chain constant region set forth in SEQ ID NO:31; the $IgG_2$ heavy chain constant region may be an $IgG_2$ heavy chain constant region set forth in SEQ ID NO: 32; the $IgG_3$ heavy chain constant region may be an $IgG_3$ heavy chain constant region set forth in SEQ ID NO:33; and the $IgG_4$ heavy chain constant region may be an $IgG_4$ heavy chain constant region set forth in SEQ ID NO: 34, but the scope of the present invention is not limited thereto.

In addition, when the monoclonal antibody that binds specifically to DLL4 comprises a light chain constant region, the light chain constant region may be of lambda ($\lambda$) or kappa ($\kappa$) light chain origin. When the light chain constant region of the monoclonal antibody is of lambda light chain origin, it may be a lambda light chain constant region set forth in SEQ ID NO: 35, but is not limited thereto.

As used herein, the term "delta-like ligand 4 (DLL4)" refers to one of delta-class ligands binding to Notch receptors and preferably refers to a protein binding to Notch 1 or Notch 2, but is not limited thereto. DLL4 may be any mammalian DLL4, but is preferably human DLL4. For the purpose of the present invention, DLL4 may refer to a protein that can either bind to Notch 1 or 4 receptor expressed in cancer cells or vascular endothelial cells to induce the growth of cancer or induce the progression of autoimmune disease, but is not limited thereto.

It is known that the DLL4 is overexpressed in various tumor cells including tumor vasculatures and is involved in proliferation and metastasis of cancer by enhancing the vascular function in tumors of cancer model. Also, it is known that the inhibition of DLL4 can treat autoimmune disease.

The DLL4 proteins include, but are not limited to, wild-type or mutant DLL4 proteins. As used herein, the term wild-type DLL4 protein generally refers to a polypeptide comprising the amino acid sequence of wild-type DLL4 protein, and the phrase amino acid sequence of wild-type DLL4 protein generally refers to an amino acid sequence found in naturally occurring DLL4. Information about DLL4 can be obtained from known databases, including GenBank of the National Institutes of Health and may be, for example, GenBank Accession Number NM_019074.3 (Gene ID: 54567), but is not limited.

As used herein, the term "Notch receptor" refers to a protein that mediates Notch signaling, and may be used interchangeably with Notch. The Notch receptor may be any protein that mediates Notch signaling. Preferably, the Notch receptor may be Notch 1 or Notch 4 receptor, but is not limited thereto. For the purpose of the present invention, the Notch receptor may be any protein that binds to mammalian DLL4, but is preferably a protein that binds to human DLL4. As used herein, the term "Notch" is meant to include all wild-type Notch or mutant Notch proteins. As used herein, the term "wild-type Notch" refers to a polypeptide comprising the amino acid sequence of wild-type Notch protein, and the phrase "amino acid sequence of wild-type Notch protein" generally refers to an amino acid sequence found in naturally occurring Notch receptor.

As used herein, the phrase "inhibiting the interaction between human delta-like ligand 4 and Notch receptor" means that the DLL4-specific monoclonal antibody of the present invention binds to DLL4 to inhibit the interaction between DLL4 and Notch receptor. Preferably, the phrase means that the DLL4-specific monoclonal antibody binds to DLL4 to inhibit the interaction between DLL4 and Notch 1 or Notch 4 receptor, but is not limited thereto. The DLL4-specific monoclonal antibody of the present invention inhibits the interaction between DLL4 and Notch receptor to prevent Notch receptors from being structurally changed by the binding of DLL4 thereto. Thus, it prevents the hydrolysis of Notch proteins to inhibit Notch signaling. It is known that when DLL4 binds to Notch receptor in tumors, it activates the signaling between vascular endothelial cells or Notch signaling between cancer stem cell and vascular endothelial cell, increases the size of blood vessels, and enhances a vascular function in tumors, thereby taking a role in the proliferation and metastasis of tumors (Ji-Liang Li et al., Cancer Res 2007; 67(23):11244-53). Thus, when Notch signaling by DLL4 in tumors is inhibited, angiogenesis cannot be easily controlled, and thus the growth of tumors can be inhibited. In addition, when DLL4 is blocked, the loss of lateral inhibition in cells at the end of an angiogenic site appears to cause excessive sprouting, resulting in a decrease in angiogenic reactions having low productivity, and perfusion for supplying oxygen can be reduced to induce hypoxia around tumors, resulting in anti-tumor effects even against tumors showing resistance to anti-VEGF therapy (Noquera-Troise I et al., Novartis Found Symp 2007; 283:106-20). Accordingly, the inventive DLL4-specific human monoclonal antibody that effectively inhibits the interaction between DLL4 and Notch can be effectively used for the treatment of cancer. In addition, it is known that the inhibition of DLL4 can stimulate the development of regulatory T cells to alleviate autoimmune diseases such as encephalomyelitis (Bassil et al., J Immunol 2011; 187(5); 2322-8). Further, it is known that a DLL4 antagonist can be used for the treatment of autoimmune disease (US Patent Publication No. 2011-0189200) and that a DLL4-binding protein such as an antibody can be used for the treatment of autoimmune disease (US Patent Publication No. 2011-0117079). Thus, the inventive antibody that effectively binds to DLL4 to inhibit the interaction between DLL4 and Notch receptor can also be effectively used for the treatment of autoimmune disease.

Figure 3A:
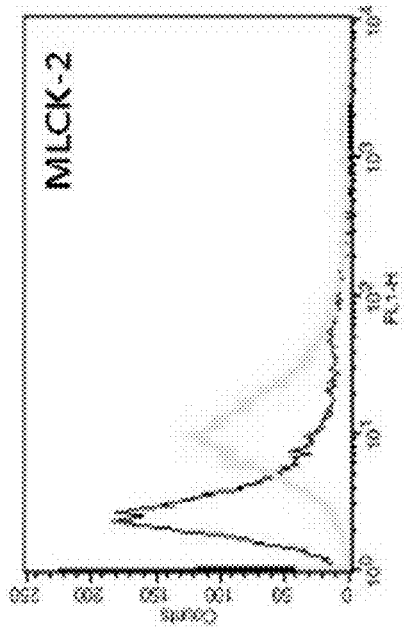
FIGS. 3A-3D show the results of flow cytometry conducted to examine the abilities of monoclonal antibodies to bind to DLL4 in HEK293 cells in which DLL4 was artificially overexpressed MLCK-1 in FIG. 3A; MLCK-2 in FIG. 3B; MLCK-3 in FIG. 3C; MLCK-4 in FIG. 3D).
Figure 3B:
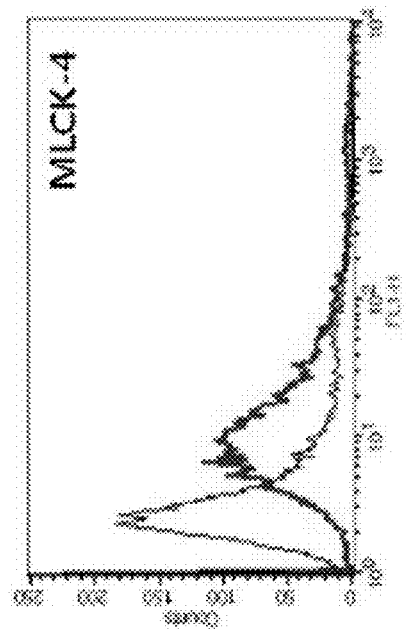
Figure 3C:
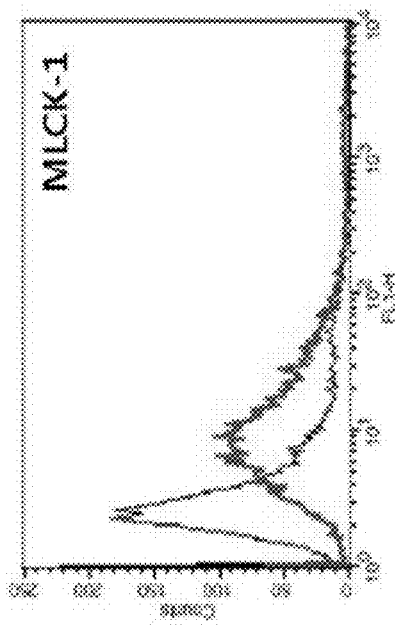
Figure 3D:
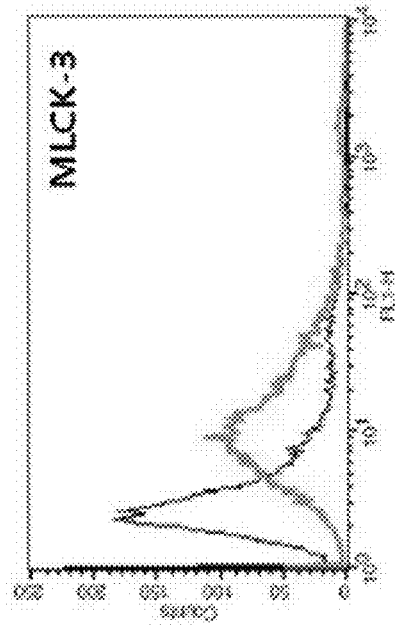
Figure 4:
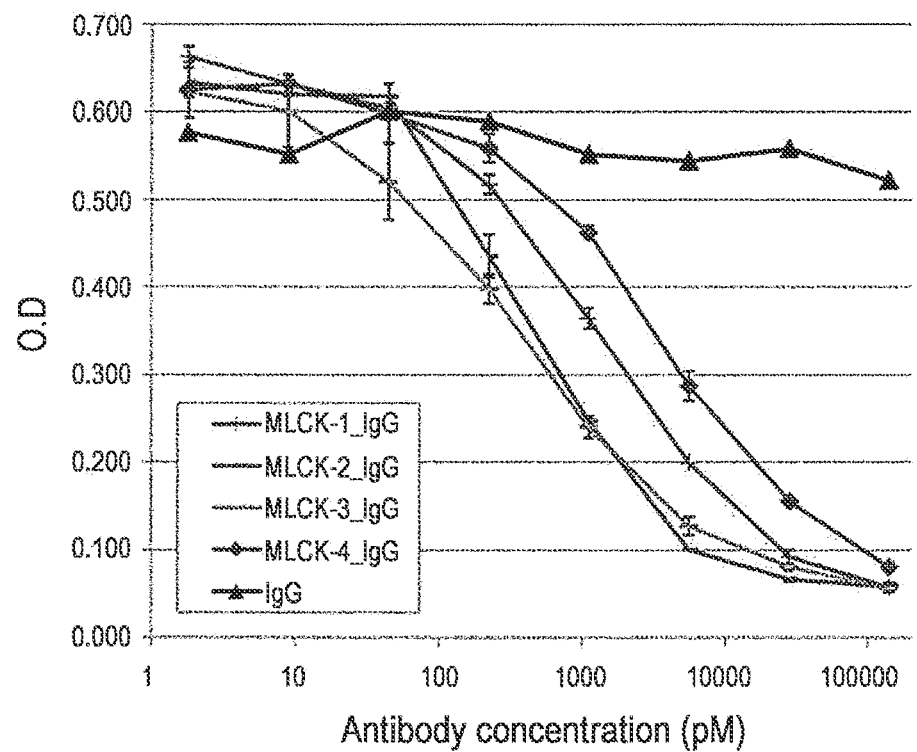
FIG. 4 shows the results of ELISA conducted to examine the abilities of monoclonal antibodies to neutralize DLL4.
Figure 5:
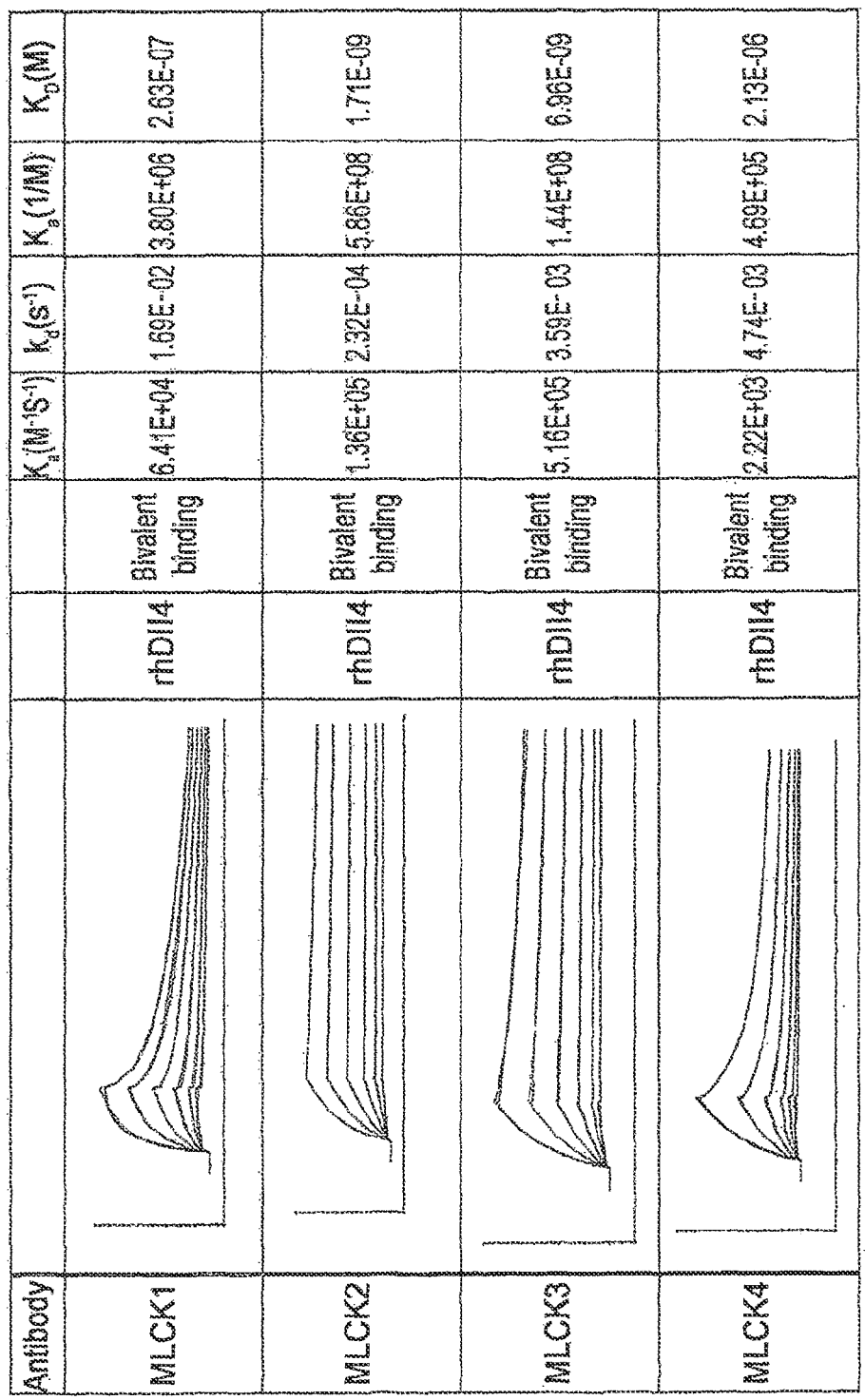
FIG. 5 shows the results of measuring the affinity of an antigen, DLL4, with anti-DLL4 antibodies of the present invention, MLCK-1, MLCK-2, MLCK-3, and MLCK-4, by using a Biacore apparatus.
Figure 6:
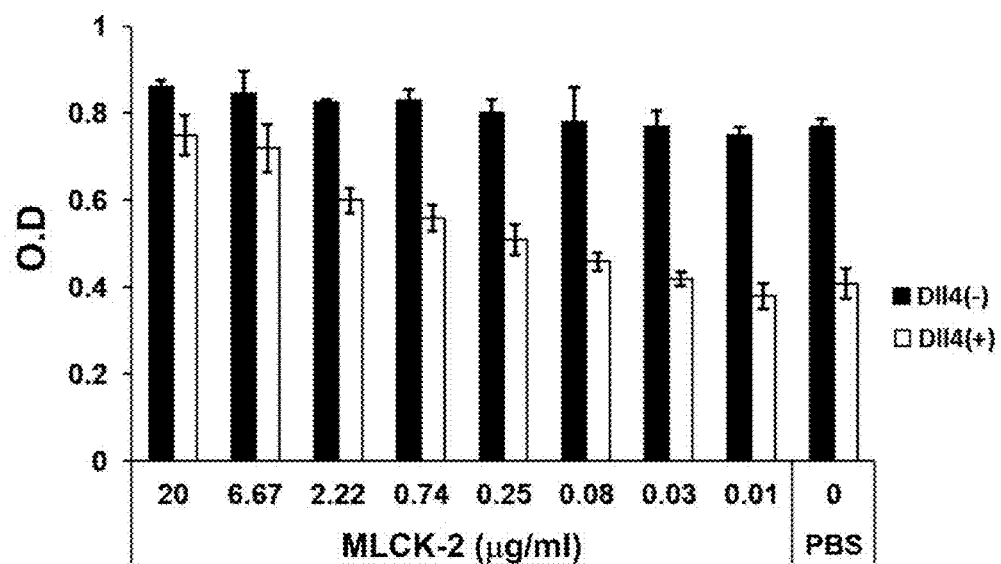
FIG. 6 demonstrates that the anti-DLL4 antibody, MLCK-2, blocks the DLL4-mediated suppression of HUVEC proliferation.
Figure 7:
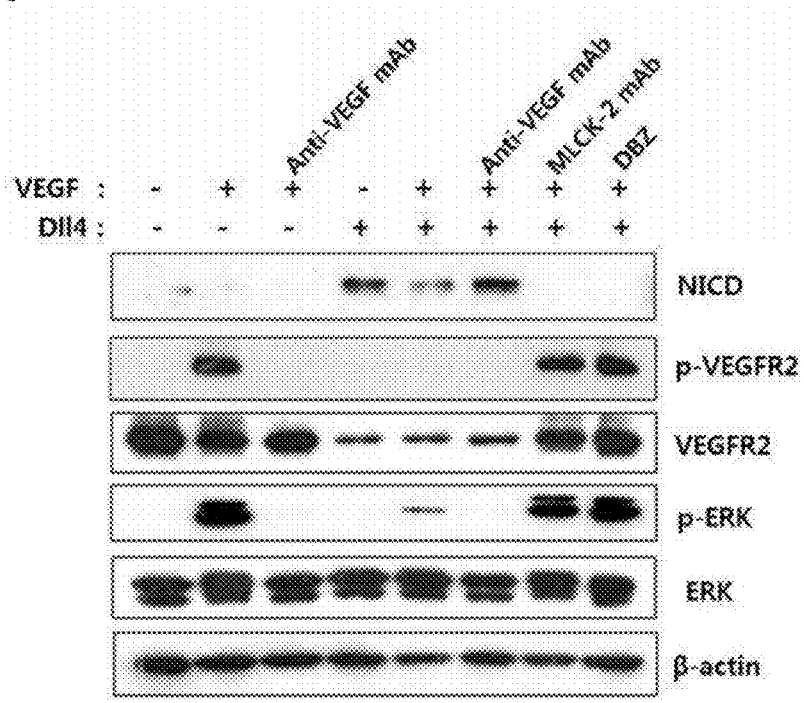
FIG. 7 shows the results of western blotting demonstrating that the anti-DLL4 antibody, MLCK-2, inhibits Notch signaling through disrupting the interaction between DLL4 and Notch.

In an example of the present invention, the DLL4-specific human monoclonal antibodies MLCK-1, MLCK-2, MLCK-3 and MLCK-4 were constructed, and it was observed that the antibodies demonstrated the binding capacity to human DLL4 with the percentage of 47.82%, 59%, 52.85% and 52.46% respectively, compared to a control (FIG. 3A, monoclonal antibody MLCK-1, FIG. 3B, monoclonal antibody MLCK-2, FIG. 3C, monoclonal antibody, MLCK-3, FIG. 3D, monoclonal antibody MLCK-4), and that these antibodies blocked most of the bindings between DLL4 and human Notch 1 receptor at a low antibody concentration of 0.1 µM (FIG. 4). Furthermore, Kn(M) of the anti-DLL4 antibodies of the present invention, MLCK-1, MLCK-2, MLCK-3, and MLCK-4, for hDLL4 were $2.63 \times 10^{-7}M$, $1.71 \times 10^{-9}M$, $6.96 \times 10^{-9}M$, and $2.13 \times 10^{-6}M$ respectively (FIG. 5). Also, the proliferation of vascular endothelial cell was inhibited by DLL4 in a concentration-dependent manner (FIG. 6). Also, activation of DLL4-Notch signaling led to an inhibition of NICD production (FIG. 7). These results suggest that the DLL4-specific human monoclonal antibodies of the present invention can provide anticancer effects and therapeutic effects against autoimmune diseases by efficiently blocking the binding between DLL4 and Notch receptor and by inhibiting Notch signaling.

In another aspect, the present invention provides a method for preparing the above-described monoclonal antibody.

The monoclonal antibody of the present invention can be easily prepared using conventional monoclonal antibody production technology. For example, the method for preparing the monoclonal antibody may be performed by producing a hybridoma using B lymphocytes obtained from immunized animals (Koeher and Milstein, 1976, Nature, 256:495) or may be performed using phage display technology, but is not limited thereto.

An antibody library using a phage display is a method of expressing an antibody on the surface of a phage with genes of the antibody directly obtained from B lymphocytes without preparation of hybridoma. Many of the difficulties associated with generating monoclonal antibodies by B-cell immortalization can be overcome by a phage display method. A conventional phage display comprises the steps of: 1) inserting an oligonucleotide having a random sequence into the region corresponding to the N-terminus of a phage coat protein pIII (or pIV); 2) expressing a fusion protein of a natural coat protein and a polypeptide coded by said oligonucleotide having a random sequence; 3) treating a receptor material that can bind to the polypeptide coded by said oligonucleotide; 4) eluting peptide-phage particles bound to the receptors using low pH or a molecule which has binding competitiveness; 5) amplifying the eluted phage in a host cell by panning; 6) repeating said steps to obtain desired amounts of phage; and 7) determining the sequence of an active peptide with the DNA sequencing of phage clones selected by panning.

In a preferred embodiment, the method for preparing the inventive monoclonal antibody may be performed by a phage display method. A person skilled in the art to which the present invention pertains can easily perform the above steps with reference to well-known phage display techniques, which are disclosed in, for example, Barbas et al. (METHODS: A Companion to Methods in Enzymology 2:119, 1991 및 J. Virol. 2001 July; 75(14):6692-9) and Winter et al. (Ann. Rev. Immunol. 12:433, 1994).

Examples of a phage which can be used for constructing the antibody library include, but are not limited to, filamentous phages such as fd, M13, f1, If1, Ike, Zj/Z, Ff, Xf, Pf1 and Pf3. Also, examples of a vector which can be used for the expression of a heterogeneous gene on the surface of the filamentous phage include, but are not limited to, phage vectors such as fUSE5, fAFF1, fd-CAT1 or fdtetDOG, or phagemid vectors such as pHEN1, pComb3, pComb8 or pSEX. Further, examples of a helper phage, which can be used to provide a natural coat protein required for successful re-infection of recombinant phage, include, but are not limited to, M13K07 and VSCM13.

A polynucleotide encoding the inventive hybridoma-derived monoclonal antibody or phase display clone can be readily isolated and sequenced using conventional procedures (e.g., by using oligonucleotide primers designed to specifically amplify the heavy chain and light chain regions of interest from a hybridoma or phage template DNA). Once the polynucleotide is isolated, it can be placed into an expression vector, which is then transfected into suitable host cells, and the desired monoclonal antibody can be prepared from the transformed host cells (i.e., transformants). Thus, the method for preparing the inventive human monoclonal antibody may comprise a step of amplifying an expression vector comprising a polynucleotide encoding the human monoclonal antibody, but is not limited thereto.

In another aspect, the present invention provides a polynucleotide encoding the monoclonal antibody, an expression vector comprising the polynucleotide, and a transformant comprising the expression vector.

The monoclonal antibody is as described above.

An expression vector comprising a polynucleotide encoding the monoclonal antibody according to the present invention is not specifically limited, but may be a vector capable of replicating and/or expressing the polynucleotide in eukaryotic or prokaryotic cells, including mammalian cells (e.g., human, monkey, rabbit, rat, hamster or mouse cells), plant cells, yeast cells, insect cells and bacterial cells (e.g., *E. coli*). Preferably, it may be a vector, which comprises at least one selective marker and is operably linked to a suitable promoter so that the polynucleotide can be expressed in a host cell. For example, the vector may comprise the polynucleotide introduced into a phage, plasmid, cosmid, mini-chromosome, virus or retrovirus vector.

The expression vector comprising the polynucleotide encoding the polynucleotide may be either an expression vector comprising the heavy chain or light chain of the monoclonal antibody or an expression vector comprising polynucleotides encoding the heavy chain and light chain of the monoclonal antibody.

Cells into which the expression vector of the present invention is to be introduced to form transformants include bacterial cells such as *E. coli*, *Streptomyces* and *Salmonella typhimurium*; yeast cells; fungal cells such as *Pichia pas-*

*toris*; insect cells such as *Drosophila* or *Spodoptera* Sf9 cells; animal cells such as Chinese hamster ovary (CHO) cells, SP2/0 (mouse myeloma), human lymphoblastoid, COS, NSO (mouse myeloma), 293T, Bowes melanoma cells, HT-1080, BHK (baby hamster kidney cells), HEK (human embryonic kidney cells), PERC.6 (human retinal cells), and the like; and plant cells.

As used herein, the term "introduction" refers to the delivery of the vector comprising the polynucleotide encoding the monoclonal antibody into a host cell. This introduction may be performed by various methods known in the art, including calcium phosphate-DNA coprecipitation, DEAE-dextran-mediated transfection, polybrene-mediated transfection, electroporation, microinjection, liposome-mediated transfection, liposome fusion, lipofection and protoplast fusion. Also, transfection means delivering a desired material into a cell by means of infection using viral particles. In addition, the vector may be introduced into a host cell by gene bombardment. In the present invention, introduction may be used interchangeably with transfection.

In another aspect, the present invention provides a pharmaceutical composition for preventing or treating cancer comprising the monoclonal antibody.

The monoclonal antibody of the present invention can bind to DLL4 to inhibit the interaction between DLL4 and Notch receptor, whereby it can be involved in the inhibition of growth of cancer. Herein, DLL4 and Notch receptor are as described above.

As used herein, the term "cancer" refers to any kind of cancer that can be treated by the monoclonal antibody of the present invention. Examples of cancer that can be treated by the monoclonal antibody include, but are not limited to, esophageal cancer, stomach cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, brain cancer, thyroid cancer, leukemia, Hodgkin's disease, lymphoma, multiple myeloma, and blood cancer.

As used herein, the term "prevention" refers to all actions that inhibit or delay the development of cancer by administering the composition, and the term "treatment" refers to all actions that restore or beneficially change the symptoms of cancer by administering the composition.

The pharmaceutical composition may further comprise a pharmaceutically acceptable carrier.

As used herein, the term "pharmaceutically acceptable carrier" refers to a carrier or diluent that does not cause significant irritation to an organism and does not abrogate the biological activity and properties of the administered compound.

Examples of pharmaceutically acceptable carriers, which can be used to formulate the inventive composition in the form of liquid solutions, include saline solution, sterile water, Ringer's solution, buffered saline solution, dextrose solution, maltodextrin solution, glycerol, ethanol, and a mixture of two or more thereof. If necessary, the inventive composition may also contain other conventional additives, such as antioxidants, buffers and bacteriostatic agents. Moreover, the inventive composition may additionally contain diluents, dispersants, surfactants, binders and lubricants in order to formulate it into injectable formulations, such as aqueous solutions, suspensions and emulsions, pills, capsules, granules and tablets.

The pharmaceutical composition may be in the form of various oral or parenteral formulations. The pharmaceutical composition is formulated using conventional diluents or excipients, including fillers, extenders, binders, wetting agents, disintegrants, and surfactants. Solid formulations for oral administration include tablets, pills, powders, granules, capsules, etc. These solid formulations may be prepared by mixing at least one compound with one or more excipients, for example, starch, calcium carbonate, sucrose, lactose, gelatin, etc. In addition to simple excipients, lubricants such as magnesium stearate or talc may also be used. In addition, liquid formulations for oral administration include a suspension, a solution, an emulsion and a syrup, etc. In addition to water commonly used as a simple diluent and liquid paraffin, various excipients, for example, wetting agents, sweetening agents, flavors, preservatives, etc. may be included. Formulations for parenteral administration include sterilized aqueous solutions, non-aqueous solvents, suspending agents, emulsions, freeze-drying agents, suppositories, etc. Propylene glycol, polyethylene glycol, vegetable oils such as olive oil, injectable esters such as ethyl oleate, etc. may be used as non-aqueous solvents and suspending agents. Bases for suppositories may include witepsol, macrogol, tween 61, cacao butter, laurin butter, glycerinated gelatin, etc.

The pharmaceutical composition may have any one formulation selected from the group consisting of a tablet, a pill, powder, granules, a capsule, a suspension, a solution, an emulsion, a syrup, a sterilized aqueous solution, a non-aqueous solution, a suspension, an emulsion, a lyophilized formulation, and a suppository.

The pharmaceutical composition of the present invention may be administered in a pharmaceutically effective amount.

As used herein, the term "pharmaceutically effective amount" refers to an amount sufficient to treat diseases, at a reasonable benefit/risk ratio applicable to any medical treatment. The effective dosage level of the composition may be determined depending on the subject's type, the disease severity, the subject's age and sex, the activity of the drug, sensitivity to the drug, the time of administration, the route of administration, excretion rate, the duration of treatment, drugs used in combination with the composition, and other factors known in the medical field. The pharmaceutical composition of the present invention may be administered alone or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this minimum amount can be easily determined by those skilled in the art.

In another aspect, the present invention provides a method for treating cancer using the monoclonal antibody.

Herein, the monoclonal antibody and cancer are as described above.

The method for treating cancer may comprise a step of administering a pharmaceutical composition comprising the monoclonal antibody together with a pharmaceutically acceptable carrier to a subject having cancer or suspected of having cancer.

Herein, the pharmaceutically acceptable carrier is as described above. Examples of the subject include mammals, including cattle, pigs, sheep, chickens, dogs, and humans.

The subject may be any subject in which cancer is to be treated by administration of the composition of the present invention.

The composition may be administered in a therapeutically effective amount in a single or multiple dosage form. Herein, the composition may be administered in the form of liquid, powder, aerosol, capsule, enteric coated tablet or capsule, or suppository. In addition, the composition may be administered intraperitoneally, intravenously, intramuscularly, subcutaneously, intradermally, orally, intranasally, intrapulmonarily or intrarectally, but is not limited thereto. However, when the composition is administered orally, the peptide is digested in the stomach, and for this reason, the oral composition should be formulated so that the active ingredient is coated or protected from decomposition in the stomach. In addition, the pharmaceutical composition may be administered using any system capable of delivering the active ingredient to a target cell.

In another aspect, the present invention provides a method for diagnosing cancer, the method comprising a step of detecting a delta-like ligand 4 (DLL4) protein in a biological sample, isolated from a subject suspected of having cancer, by an antigen-antibody reaction using the above-described monoclonal antibody.

Herein, the monoclonal antibody, the cancer, the individual and the DLL4 protein are as described above.

In the method for diagnosing cancer, the DLL4 protein can be detected by reacting the inventive DLL4-specific monoclonal antibody with the biological sample isolated from the individual suspected of having cancer, and detecting the formation of an antigen-antibody complex, whereby information for diagnosis of cancer can be provided or cancer can be diagnosed. Because DLL4 is overexpressed in various cancer cells, including ovarian cancer cells (Wei Hu et al., Cancer Res 2011; 71:6030-6039.), cancer can be diagnosed by comparing the expression level of DLL4 in the biological sample with that in a control group such as a normal cell or tissue, but is not limited thereto.

Specifically, the method for diagnosing cancer may be a method for either providing information for diagnosis of cancer or diagnosing cancer, the method comprising the steps of: (a) treating a biological sample, isolated from a subject suspected of having cancer, with the above-described monoclonal antibody, to detect a DLL4 protein by an antigen-antibody reaction; and (b) comparing the level of the DLL4 protein detected in step (a) with that in a control group, and judging the subject to have cancer if the level of the DLL4 protein in the biological sample is higher than that in the control group.

As used herein, the term "biological sample" is meant to include tissue, a cell, whole blood, serum, plasma, a tissue autopsy samples (brain, skin, lymph node, spinal cord, etc.), a cell culture supernatant, a ruptured eukaryotic cell, and a bacterial expression tissue, but is not limited thereto. These biological samples can be reacted with the inventive monoclonal antibody in a manipulated or non-manipulated state in order to determine the presence of the DLL4 protein or the presence or absence of cancer.

As used herein, the term "antigen-antibody complex" refers to a conjugate between the DLL4 protein antigen in the sample and the inventive monoclonal antibody recognizing the DLL4 protein antigen. The formation of this antigen-antibody complex can be detected by any method selected from the group consisting of a colorimetric method, an electrochemical method, a fluorimetric method, luminometry, a particle counting method, visual assessment, and a scintillation counting method, but is not limited thereto, and various methods may be used.

In the present invention, various labels may be used to detect the antigen-antibody complex. Specific examples of the label include, but are not limited to, enzymes, fluorescent materials, ligands, luminescent materials, microparticles, and radioactive isotopes.

Examples of the enzyme that is used as the detection label include acetyl-cholinesterase, alkaline phosphatase, βD-galactosidase, horseradish peroxidase, and β-latamase. Examples of the fluorescent material include $Eu^{3+}$, $Eu^{3+}$ chelator, cryptate and the like. Examples of the ligand include biotin derivatives and the like, and examples of the luminescent material include acridinium ester, isoluminol derivatives and the like. In addition, examples of the microparticles include colloidal gold, colored latex, etc., and examples of the radioactive isotope includes $^{57}Co$, $^{3}H$, $^{125}I$, and $^{125}I$-Bonton Hunter reagents.

Preferably, the antigen-antibody complex may be detected by an ELISA method. Examples of the ELISA method include direct ELISA using a labeled antibody recognizing an antigen attached to a solid support, indirect ELISA using a labeled secondary antibody recognizing a capture antibody in an antibody complex that recognizes an antigen attached to a solid support, direct sandwich ELISA which comprises using a labeled antibody to recognize an antigen in an antigen-antibody complex attached to a solid support, and indirect sandwich ELISA which comprises reacting an antibody with an antigen in an antigen-antibody complex attached to a solid support and then reacting a labeled secondary antibody with the reacted antibody.

The monoclonal antibody may have a detection label. If the monoclonal antibody has no detection label, it can be captured and detected by treatment with another antibody having a detection label.

In another aspect, the present invention provides a composition for diagnosing cancer comprising the above-described monoclonal antibody.

Herein, the monoclonal antibody and the cancer are as described above.

The diagnostic composition comprising the inventive DLL4-specific monoclonal antibody can be used to diagnose the expression of DLL4, a disease related to the expression level of DLL4 or a DLL4-mediated disease such as cancer.

In still another aspect, the present invention provides a kit for diagnosing cancer comprising the above-described diagnostic composition.

Herein, the composition and the cancer are as described above.

In addition, the kit for diagnosing cancer may further comprise a composition, a solution or a device, which has one or more other components suitable for analysis.

In still another aspect, the present invention provides a pharmaceutical composition for preventing or treating autoimmune disease comprising the above-described monoclonal antibody.

Herein, the monoclonal antibody, prevention and treatment are as described above. In addition, the pharmaceutical composition may further comprise a pharmaceutically acceptable carrier. Herein, the pharmaceutical composition is as described above.

As used herein, the term "autoimmune disease" collectively refers to diseases that are directly or indirectly caused by an immune response to the antigen of a diseased subject. Examples of autoimmune disease include rheumatoid arthritis, systemic sclerosis, systemic Lupus erythematosus, atopic dermatitis, psoriasis, alopecia areata, asthma, Crohn's disease, Behcet's disease, Sjogren's syndrome, Gillaine-Barre syndrome, chronic thyroiditis, multiple sclerosis, polymyositis, ankylosing spondylitis, encephalomyelitis, fibrositis, and polyarteritis nodosa.

As described above, the DLL4-specific human monoclonal antibody of the present invention can stimulate the development of regulatory T cells, and thus can be used for the treatment of autoimmune disease.

In still another aspect, the present invention provides a method for treating autoimmune disease using the above-described monoclonal antibody.

Specifically, the method for treating autoimmune disease may comprise a step of administering a pharmaceutical composition comprising the monoclonal antibody together with a pharmaceutically acceptable carrier to a subject having or suspected of having autoimmune disease. Herein, the autoimmune disease, the subject and the pharmaceutically acceptable carrier are as described above.

MODE FOR THE INVENTION

Hereinafter, the present invention will be described in more detail with reference to Examples. It is to be understood, however, that these examples are for illustrative purposes only and are not intended to limit the scope of the present invention.

Example 1

Preparation of Anti-DLL4 Antibody

Example 1-1

Preparation of DLL4 Antigen

The antigen of human DLL4 extracellular domain used in this Example was human DLL4 protein (Cat: 1506-D4/CF) purchased from R&D System. The DLL4 antigen protein comprises 27th to 522nd amino acid residues of DLL4. Also, the C-terminal of the protein was tagged with histidine.

Then, another antigen for a specific region of the DLL4 extracellular domain was prepared. The specific region comprises 27th to 251st amino acid residues of DLL4. This region comprises a motif called delta/serrate/lag-2 (DSL) domain which is known to bind with a Notch 1 receptor (Tax et al., 1994, Nature 368:150-4). A mammalian expression plasmid vector comprising a CMV promoter upstream of a polynucleotide encoding a deletion fragment of the DLL4 extracellular domain fused with a Fc protein was prepared by using a standard recombinant DNA technique. An additional construct encoding a deletion fragment of DLL4, which is a chimera of human DLL4 fused with a Fc protein, was also prepared by using a standard recombinant DNA technique. The recombinant fusion proteins comprising 27th to 251st amino acid residues of human DLL4 fused with Fc protein were transiently transfected to HEK 293E cells and expressed in the cells. For preparing the antigen protein, conditioning media were collected every 72 hours, and this process was repeated four times. The antigen protein was purified from the conditioning medium through protein A affinity chromatography.

Example 1-2

Preparation of Library Phage

The 10 g/ml of recombinant human DLL4 solution (R&D System) was added to an immunotube, and the DLL4 proteins were adsorbed onto the surface of the immunotube at 4° C. overnight. Then, 1% bovine serum albumin (BSA) solution was added to the immunotube to protect the area of surface where DLL4 was not adsorbed to. After evacuating the immunotube, $10^{12}$ CFU of antibody phage library dispersed in 1% BSA solution were added thereto so they can bind to the antigen. The immunotube was washed five times with phosphate buffered saline-0.05% Tween 20 (PBS-T) solution to remove non-specifically bound phages, and the remaining antigen-specific phage antibodies were collected by using 100 mM triethylamine solution. The collected phases were neutralized with IM Tris buffer (pH 7.4), and then transfected into *E. coli* ER2537 at 37° C. for 1 hour. The transfected *E. coli* cells were plated onto carbenicillin-containing Luria-Bertani (LB) agar medium and cultured at 37° C. overnight. On the next day, the cultured *E. coli* cells were suspended in 4 ml of superbroth (SB)-carbenicillin medium, and 15% glycerol was added thereto. Then, a portion of the cell suspension was stored at −80° C., and 50 μl of the remainder was incubated at 37° C. in 20 ml of SB-carbenicillin medium supplemented with 2% glucose solution. When the absorbance of the cell culture reached 0.6 at 600 nm, the culture medium was removed by centrifugation, and the remaining cell pellet was suspended again in 20 ml of SB-carbenicillin medium and added with $10^{12}$ PFU of VCSM13 helper phage. Then the cell culture was incubated with slow stirring at 37° C. On the next day, the cell culture was centrifuged, and only the culture medium was collected and added with 4% polyethyleneglycol 8000 (PEG 8000) and 3% sodium chloride (NaCl) and settled at 4° C. for 30 minutes, followed by centrifugation. The supernatant was removed, and the precipitated phage was suspended in 1 ml of PBS. Using this suspension as a library, the above panning process was repeated to amplify and concentrate the antigen-specific clones.

Example 1-3

Panning by Phage Display

In order to screen an antibody that binds to the Notch 1-binding site in human DLL4 protein, cross-panning of human DLL4 protein and a deletion fragment (27th to 251st amino acid residues) corresponding to a specific region of human DLL4 protein was performed for 3 rounds. Then, the cells were plated and cultured on LB-carbenicillin agar media containing an antibody gene to obtain single colonies, which were then inoculated and incubated in 400 μl of SB-carbenicillin medium, after which the expression of scFv-type protein in the periplasm of *E. coli* was induced by adding IPTG. The *E. coli* cells were suspended in TES solution (Tris,EDTA,sucrose) and allowed to stand at 4° C. for 1 hour. Then, the suspension was centrifuged to extract the periplasm, which was then used to examine the binding between the recombinant human DLL4 antigen and scFv by an ELISA technique (Steinberger. Rader and Barbas III. 2000. Phage display vectors. In: Phage Display Laboratory Manual. 1sted. Cold Spring Harbor Laboratory Press. NY. USA. pp. 11.9-11.12). The bound scFv was detected using a horseradish peroxidase (HRP)-anti-HA antibody and a tetramethylbenzidine (TMB) substrate. The detected antigen-specific antibody clones were sequenced.

Example 2

Assay for Binding Affinity of Anti-DLL4 Antibody for DLL4

The antibodies, isolated and purified in Example 1, were named "MLCK-1", "MLCK2", "MLCK-3" and "MLCK-4", respectively, and were found to comprise a heavy chain variable region of SEQ ID NO: 1 and a light chain variable region of SEQ ID NO: 15 (MLCK-1), a heavy chain variable region of SEQ ID NO: 5 and a light chain variable region of SEQ ID NO: 19 (MLCK-2), a heavy chain variable region of SEQ ID NO: 8 and a light chain variable region of SEQ ID NO: 23 (MLCK-3), and a heavy chain variable region of SEQ ID NO: 11 and a light chain variable region of SEQ ID NO: 27 (MLCK-4), respectively. The affinities of the isolated antibodies to the antigen were analyzed in the following manner.

The anti-DLL4 antibody-antigen binding affinity was evaluated using an ELISA-based binding test. A 96-well microtiter plate (Nunc-Immuno Plate, NUNC, Rochester, N.Y.) was coated with 2 μg/ml of hDLL4-His protein in PBS solution at 4° C. overnight, and non-specific binding sites were blocked with BSA (bovine serum albumin) for 2 hours. The anti-DLL4 antibody (purified protein) on the 96-well microtiter plate was transferred to a microtiter plate at an antibody concentration ranging from 0 nM to 128 nM. Then, the plate was incubated for 2 hours, after which the plate was washed five times with 0.05% tween 20-containing PBS, and in order to detect the plate-bound DLL4 antibody, an HRP-conjugated Fab polyclonal antibody reagent (Pierce) was diluted at a ratio of 1:10,000, transferred to the washed microtiter plate, and then allowed to react at 37° C. for 1 hour. After the reaction, color development was performed using a colorimetric substrate (3,3',5,5'-tetramethylbenzidine; Sigma-Aldrich Co.). The enzymatic reaction was stopped using 0.5 mol/l of sulfuric acid, and the absorbance at 450 nm-650 nm was recorded using a microplate reader (molecular device). As a result, it was shown that the binding affinities of the antibodies for DLL4 increased in a concentration-dependent manner (FIG. 2).

Example 3

Measurement of the Ability of Anti-DLL4 Antibodies Bind to DLL4 Ligand

The ability of the anti-DLL4 antibodies to bind DLL4 was measured by FACS analysis together with ELISA.

Specifically, human embryonic kidney cells (HEK 293) that stably express human DLL4 were prepared, and the degree of binding of the anti-DLL4 antibodies to DLL4 was measured using the prepared cells and a FACSCalibur system (BD Biosciences). The HEK293 cells that stably expressed DLL4 were dissociated, washed with PBS, adjusted to a cell number of $1\times10^5$ cells/200 μl PBS, treated with 10 μg of each of the DLL4 monoclonal antibodies, and then allowed to react at room temperature for 30 minutes. After the reaction, the cells were washed with PBS and reacted with an FITC-labeled Fc-specific antibody (goat anti-human IgG FITC conjugate, Fc specific, Sigma, F9512; concentration: 2.0 mg/ml) at a concentration of 5 μl/$1\times10^5$ cells/200 μl PBS at 4° C. for 1 hours. After the reaction, the cells were washed with PBS and analyzed using a FACSCalibur system. A control group was treated only with an FITC-labeled Fc-specific antibody. The results of analysis of human DLL4-minoclonal antibody-FITC binding in the test group treated with each of the DLL4 monoclonal antibodies were compared with those in the control group.

The results of measuring the degree of each of the monoclonal antibodies to human DLL4 antigen are shown in FIGS. 3A-3D. As can be seen in FIGS. 3A-3D, the degrees of binding of the monoclonal antibodies to DLL4 antigen compared to the control group were as follows: MLCK-1: 47.82% (FIG. 3A); MLCK-2: 59% (FIG. 3B); MLCK-3: 52.85% (FIG. 3C); and MLCK-4: 52.46% (FIG. 3D).

Such results suggest that the MLCK-1, MLCK-2, MLCK-3 and MLCK-4 antibodies of the present invention have high binding affinities for human DLL4.

Example 4

Assay for Neutralization Effects of Anti-DLL4 Antibodies

The neutralization effects of the anti-DLL4 antibodies were evaluated using an ELISA-based solution competition test.

Each well of a 96-well microtiter plate (Nunc-Immuno Plate, NUNC, Rochester, N.Y.) was coated with 100 μl of 500 ng/ml of hNotch-1-hFc protein (R&D Systems) (diluted in PBS) at 4° C. overnight, and non-specific binding sites were blocked with BSA for 2 hours.

The anti-DLL4 antibody (purified protein) on the 96-well microtiter plate was premixed with serial dilutions of antigen protein (DLL4 antigen, 600 ng/m) at an antibody concentration ranging from 0 nM to 140 nM. The antigen/antibody mixture was incubated for 30 minutes, and then transferred to a microtiter plate precoated with the DLL4 receptor hNotch-1 protein (50 ng/well) in order to measure free antibody. Then, the plate was incubated for 2 hours and washed five times with 0.05% tween 20-containing PBS. In order to detect the DLL4 antigen bound to the plate, an HRP-conjugated His anti-mouse IgG polyclonal antibody reagent (Roche applied science) was diluted at a ratio of 1:500, and the washed microtiter plate was treated with the diluted antibody reagent, and then allowed to react at 37° C. for 1 hour. Then, color development was performed using a colorimetric substrate (3,3',5,5'-tetramethylbenzidine; Sigma-Aldrich Co.), and the enzymatic reaction was stopped using 0.5 mol/l of sulfuric acid. The absorbance at 450 nm-650 nm was measured, and the results of the measurement are shown in FIG. 4. The amounts of antibodies required to achieve a 50% decrease in human DLL4-His bound to plate-coated Notch 1-Fc ($IC_{50}$) are shown in Table 1 below.

TABLE 1

| Clone | $IC_{50}$(nM) |
|---|---|
| MLCK-1 | 1.32 |
| MLCK-2 | 0.41 |
| MLCK-3 | 0.38 |
| MLCK-4 | 3.72 |

As a result, the four antibodies of the present invention all showed an $IC_{50}$ value of 0.4-3.7 nM, suggesting that these antibodies can inhibit the binding of human Notch-1 to DLL4 ligand at a very low concentration (FIG. 4 and Table 1). Such results indicate that the four antibodies of the present invention can inhibit the growth of cancer cells by inhibiting the interaction between DLL4 ligand and Notch.

Example 5

Analysis of Binding Capacity of Anti-DLL4 Antibody

A Biacore assay was performed to determine the binding capacity of anti-DLL4 antibody.

To be specific, Biacore T200 was used in SPR analysis and HBS-EP (10 mM HEPES, pH7.4, 150 mM NaCl, 3 mM EDTA, 0.15% surfactant P20) was used as a running buffer. Surface preparation was done by using a surface preparation target immobilization tool of a wizard program (condition: 25° C., 5 µl/min). A ligand, hDLL4, was diluted in 10 mM sodium acetate (pH 4.5) to a final concentration of 10 µg/ml, and then immobilized to the surface of CM5 chip by a target immobilization level for each test group. In the immobilization process, two flow cells were included as one set wherein the first flow cell was set as a blank and the second flow cell has hDLL4 immobilized to the surface thereof in the present experiment. The first flow cell acted as a reference to account for experimental variability due to nonspecific bindings and buffer effects, and in the analysis, subtracted RU values (Fc2-Fc1) were used as experimental results. Anti-DLL4 antibodies that bind to hDLL4, i.e., MLCK1, MLCK2, MLCK-3, and MLCK4, were diluted in a running buffer to a final molar concentration of 100 nM, serially diluted 5 times, and each of the 5 dilutions was analyzed. The sample to be analyzed was prepared to have high purity and high concentration, enough to be diluted more than 100 times at minimum, thereby minimizing buffer effect. All analysis was done by using a wizard program, screening duplicates for each sample and a regeneration step was included in between each analysis step, so that the standard of experiment remains constant. The experimental results were analyzed by Biaevaluation software version 4.0. At this time, to determine the RU values (Fc2-Fc1 and Fc4-Fc3), the baseline was set to zero, the value measured at a buffer injection part (analyte, 0 nM) was subtracted from a whole sensorgram. Then, the resulting RU value was analyzed by a 1:1 binding model to determine a binding affinity. The factors to be analyzed include $k_a(M^{-1}s^{-1})$, $k_d(s^{-1})$, $K_a(1/M)$, and $K_D(M)$. To be specific, $k_a$ is an association constant demonstrating a binding affinity, and $k_d$ is a dissociation constant demonstrating stability. Equilibrium dissociation constant $K_D(M)$ was calculated by dividing $k_d$ with $k_a$ ($k_d/k_a$).

As a result, as shown in FIG. 5, $K_D(M)$ of MLCK-1 antibody for hDLL4 was $2.63\times10^{-7}$M, $K_D(M)$ of MLCK-2 antibody was $1.71\times10^{-9}$M, $K_D(M)$ of MLCK-3 antibody was $6.96\times10^{-9}$M, and $K_D(M)$ of MLCK-4 antibody was $2.13\times10^{-6}$M.

Example 6

Analysis of the Effect of Anti-DLL4 Antibody on Proliferation of Human Umbilical Vein Endothelial Cell (HUVEC)

In order to investigate the effect of DLL4-binding antibodies on proliferation of human umbilical vein endothelial cell (HUVEC), a representative anti-DLL4 antibody, MLCK-2 antibody, was analyzed for the effect thereof on proliferation of HUVEC.

To be specific, human umbilical vein endothelial cell (HUVEC) was purchased from Lonza to be used in this experiment. T-flask (Nunc) was coated with PBS buffer (Gibco) added with 1% gelatin (Sigma) at a room temperature for 4 to 6 hours, washed with PBS, and then it was used for culturing HUVECs. EBM-2 (Lonza) supplemented with EGM-2 Single Quot (Lonza) was used as a culture medium, density of a cell culture was remained below 80%, and the cells were cultured at 37° C. in a 5% $CO_2$ incubator. The cells before passage 6 were used for this experiment. HUVEC proliferation assay was done by following process. First, to prepare the hDLL4-coated plate, one day before conducting the experiment, rhDLL4 (R&D systems) was diluted in a carbonate buffer to a final concentration of 1 µg/ml in a 96-well plate (BD), where 100 µl of the diluted rhDLL4 was inoculated per each well, and the plate was incubated at 4° C. overnight. In addition, HUVEC was cultured in EBM-2 minimal medium supplemented with 0.1% FBS for 24 hours to minimize the serum effect. On the first day of experiment, each well of the rhDLL4-coated plate was washed with PBS twice, and for each test group, MLCK-2 mAb (20 µg/ml) which was diluted with the EBM-2 minimal medium was added to each well in triplicate and incubated at a room temperature for 20 minutes. The HUVECs starved for 24 hours were dissociated into single cells, and diluted to $4\times10^3$ cells/well with EBM-2 minimal medium. The diluted cells were inoculated in the well treated with antibody and incubated at 37° c. in a 5% $CO_2$ incubator for 96 hours. Once the cell proliferation is finished, 10 µl of cell counting kit-8 (CCK-8, Dojino) was added to each well and the plate was incubated at 37° c. in a 5% $CO_2$ incubator for 5 hours. Using the apparatus SpectraMax 190 (Molecular Devices), the absorption of the sample at 450 nm-650 nm was measured and the levels of cell proliferation were compared among different test groups.

As a result, as shown in FIG. 6, the representative anti-DLL4 antibody of the present invention blocked the DLL4-mediated inhibition of HUVEC proliferation in a concentration-dependent manner.

Example 7

Analysis of Inhibitory Activity of Anti-DLL4 Antibody on DLL4/Notch Signaling Pathway In Notch signaling, when DLL4 binds to a Notch receptor, this causes a constitutional change in the Notch receptor leading to the cleavage thereof, and then an intracellular domain of Notch (NICD) enters the nucleus and mediates a Notch signaling. In this regard, it was confirmed whether the anti-DLL4 antibody of the present invention could inhibit the binding between DLL4 and a Notch receptor, thereby disrupting the Notch signaling through monitoring the inhibition of a Notch receptor cleavage as below.

To be specific, in order to determine the inhibitory activity of the DLL4-binding antibodies against the DLL4/Notch signaling pathway, the inhibition of signaling pathway in HUVECs was analyzed in the present experiment. One day before conducting experiment, a recombinant human DLL4 (rhDLL4, R&D systems) was diluted with carbonate buffer to a final concentration of 1 µg/ml, and then 1 ml/well of the diluted rhDLL4 was added to a 6-well plate (BD) and incubated at 4° C. overnight. For a control group that was untreated with rhDLL4, 1 ml/well of carbonate buffer was only added to the plate and incubated at 4° C. overnight. On the next day, the DLL4-coated plate was taken from 4° c.

refrigerator and washed with PBS once, and 1 ml of EGM-2 medium was added to each well of the plate. Then, each of the antibodies, 20 μg/ml anti-VEGF mAb, 0.08 nM DBZ, and 20 μg/ml MLCK-2 mAb, was added to each well of a test group. The final volume of medium in each well was 2 ml and the added volume of antibody was twice the volume of the medium. The plate was incubated for 20 minutes. During antibody treatment, the 75T plate containing HUVECs in passages #2 to #5 was taken and after removing the medium from the plate, the cells were dissociated into single cells. Through centrifugation, HUVECs were washed and resuspended in a fresh EGM-2 medium. After counting the cells, the samples were diluted to $5 \times 10^5$ cells/ml and 1 ml of the cell sample was inoculated into each well and incubated at 37° c. in a 5% $CO_2$ incubator for one day. After culturing HUVECs, the medium was removed in each well, and the cells were washed with PBS once and treated with 2 ml of EBM-2 minimal medium including 0.2% FBS. Also, each well was added with each of the same concentration of antibodies, 20 μg/ml anti-VEGF mAb, 0.08 nM DBZ, and 20 μg/ml MLCK-2 mAb which were treated the day before, and the cells were incubated at 37° c. in a 5% $CO_2$ incubator for one day. Then, each well containing the HUVECs treated with antibodies was treated with 100 ng/ml of hVEGF (R&D systems) and incubated at 37° c. in a 5% $CO_2$ incubator for 5 minutes. Then the plate was taken out and the medium was removed quickly. The cells were washed with PBS once, and 150 μl of a cell dissolving buffer (1% NP-40, 20 mM Tris, 137 mM NaCl, 10% Glycerol, 2 mM EDTA, 1 mM Sodium orthovanadate, 1x Protease & phosphatase inhibitor cocktail) was added to each well and the plate was shaken to spread the dissolving buffer.

Subsequently, the plate was put on ice and HUVECs were collected from each well using a scraper and put into a 1.5 ml tube and stored in ice. Every 5 minutes, the 1.5 ml tube containing cell was vortexed three times and put on ice again for cell dissolving. Then the sample was centrifuged at 4° c. and 14000 rpm for 10 minutes and the isolated supernatant was transferred to a new tube and weighted. For SDS-PAGE analysis, the supernatant was added to 5×SDS sample buffer and boiled at 100° c. for 10 minutes analyzed by SDS-PAGE. At this time, the prepared protein samples were run through 4% to 12% bis-TRIS gel, separated according to their size, and the separated proteins were western blotted with the following antibodies: NICD (Cell signaling), P-ERK (Cell signaling), ERK (Cell signaling), VEGFR2 (Cell signaling), P-VEGFR2 (Cell signaling), and Actin (Santa Cruz).

As a result, as shown in FIG. 7, the cell treatment with a representative antibody of the present invention, MLCK-2 mAb, reduced the level of NICD (lane 7) which was previously increased by DLL4 treatment (lanes 4 and 5).

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A monoclonal antibody that binds specifically to human delta-like ligand 4 (DLL4) to inhibit an interaction between human delta-like ligand 4 (DLL4) and Notch receptor, wherein the monoclonal antibody comprises:

a heavy chain variable region comprising the heavy chain CDR1 amino acid sequence set forth in SEQ ID NO: 2; the heavy chain CDR2 amino acid sequence set forth in SEQ ID NO: 3; and the heavy chain CDR3 amino acid sequence set forth in SEQ ID NO: 4; and a light chain variable region comprising the light chain CDR1 amino acid sequence set forth in SEQ ID NO: 16; the light chain CDR2 amino acid sequence set forth in SEQ ID NO: 17; and the light chain CDR3 amino acid sequence set forth in SEQ ID NO: 18;

a heavy chain variable region comprising the heavy chain CDR1 amino acid sequence set forth in SEQ ID NO: 2; the heavy chain CDR2 amino acid sequence set forth in SEQ ID NO: 6; and the heavy chain CDR3 amino acid sequence set forth in SEQ ID NO: 7; and a light chain variable region comprising the light chain CDR1 amino acid sequence set forth in SEQ ID NO: 20; the light chain CDR2 amino acid sequence set forth in SEQ ID NO: 21; and the light chain CDR3 amino acid sequence set forth in SEQ ID NO: 22;

a heavy chain variable region comprising the heavy chain CDR1 amino acid sequence set forth in SEQ ID NO: 2; the heavy chain CDR2 amino acid sequence set forth in SEQ ID NO: 9; and the heavy chain CDR3 amino acid sequence set forth in SEQ ID NO: 10; and a light chain variable region comprising the light chain CDR1 amino acid sequence set forth in SEQ ID NO: 24; the light chain CDR2 amino acid sequence set forth in SEQ ID NO: 25; and the light chain CDR3 amino acid sequence set forth in SEQ ID NO: 26; or a heavy chain variable region comprising the heavy chain CDR1 amino acid sequence set forth in SEQ ID NO: 12; the heavy chain CDR2 amino acid sequence set forth in SEQ ID NO: 13; and the heavy chain CDR3 amino acid sequence set forth in SEQ ID NO: 14; and a light chain variable region comprising the light chain CDR1 amino acid sequence set forth in SEQ ID NO: 28; the light chain CDR2 amino acid sequence set forth in SEQ ID NO: 29; and the light chain CDR3 amino acid sequence set forth in SEQ ID NO: 30.

2. The monoclonal antibody of claim 1, wherein the monoclonal antibody comprises the amino acid sequence of a heavy chain variable region set forth in SEQ ID NO: 1 and the amino acid sequence of a light chain variable region set forth in SEQ ID NO: 15.

3. The monoclonal antibody of claim 1, wherein the monoclonal antibody comprises the amino acid sequence of a heavy chain variable region set forth in SEQ ID NO: 5 and the amino acid sequence of a light chain variable region set forth in SEQ ID NO: 19.

4. The monoclonal antibody of claim 1, wherein the monoclonal antibody comprises the amino acid sequence of a heavy chain variable region set forth in SEQ ID NO: 8 and the amino acid sequence of a light chain variable region set forth in SEQ ID NO: 23.

5. The monoclonal antibody of claim 1, wherein the monoclonal antibody comprises the amino acid sequence of a heavy chain variable region set forth in SEQ ID NO: 11 and the amino acid sequence of a light chain variable region set forth in SEQ ID NO: 27.

6. A pharmaceutical composition for treating cancer, comprising the monoclonal antibody of claim 1.

7. The pharmaceutical composition of claim 6, wherein the cancer is selected from the group consisting of esophageal cancer, stomach cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, brain cancer, thyroid cancer, leukemia, Hodgkin's disease, lymphoma and multiple myeloma blood cancer.

8. A method for treating cancer in a subject, comprising administering the monoclonal antibody of claim 1 to said subject that has cancer.

9. A composition for diagnosing cancer, comprising the monoclonal antibody of claim 1.

10. A method for diagnosing cancer in a subject, comprising (i) isolating a biological sample from a subject suspected of having cancer, (ii) contacting the biological sample with the antibody of claim 1 to detect delta-like ligand 4 (DLL4), and (iii) comparing the level of DLL4 protein detected in step (ii) with that of a control sample, wherein said subject has cancer if the level of DLL4 protein in the biological sample is higher than the level of DLL4 protein in the control sample.

11. A pharmaceutical composition for treating an autoimmune disease, comprising the monoclonal antibody of claim 1.

12. The pharmaceutical composition of claim 11, wherein the autoimmune disease is selected from the group consisting of rheumatoid arthritis, systemic sclerosis, systemic Lupus erythematosus, atopic dermatitis, psoriasis, alopecia areata, asthma, Crohn's disease, Behcet's disease, Sjogren's syndrome, Guillaine-Barre syndrome, chronic thyroiditis, multiple sclerosis, polymyositis, ankylosing spondylitis, encephalomyelitis, fibrositis, and polyarteritis nodosa.

13. A method for treating an autoimmune disease in a subject, comprising administering the monoclonal antibody of claim 1 to said subject that has an autoimmune disease.

* * * * *

UNITED STATES PATENT AND TRADEMARK OFFICE
CERTIFICATE OF CORRECTION

PATENT NO. : 9,598,483 B2  
APPLICATION NO. : 14/412419  
DATED : March 21, 2017  
INVENTOR(S) : Eun A. Kim et al.

Page 1 of 1

It is certified that error appears in the above-identified patent and that said Letters Patent is hereby corrected as shown below:

In the Specification

Column 16, Line 5: "The 10 g/ml of" should be --The 10 µg/ml of--.

Column 16, Line 19: "with IM Tris" should be --with 1M Tris--.

Column 17, Line 10: "MLCK2" should be --MLCK-2--.

Column 18, Line 33: "600 ng/m" should be --600 ng/ml--.

Signed and Sealed this  
Second Day of May, 2017

Michelle K. Lee  
*Director of the United States Patent and Trademark Office*